(12) United States Patent
Laudenslager et al.

(10) Patent No.: US 11,284,941 B2
(45) Date of Patent: *Mar. 29, 2022

(54) LASER ABLATION CATHETERS HAVING EXPANDED DISTAL TIP WINDOWS FOR EFFICIENT TISSUE ABLATION

(71) Applicant: RA MEDICAL SYSTEMS, INC., Carlsbad, CA (US)

(72) Inventors: James B. Laudenslager, San Marcos, CA (US); Dean S. Irwin, Carlsbad, CA (US)

(73) Assignee: RA MEDICAL SYSTEMS, INC., Carlsbad, CA (US)

(*) Notice: Subject to any disclaimer, the term of this patent is extended or adjusted under 35 U.S.C. 154(b) by 147 days.

This patent is subject to a terminal disclaimer.

(21) Appl. No.: 16/734,202

(22) Filed: Jan. 3, 2020

(65) Prior Publication Data

US 2020/0138517 A1 May 7, 2020

Related U.S. Application Data

(63) Continuation of application No. 15/359,412, filed on Nov. 22, 2016, now Pat. No. 10,555,772.

(60) Provisional application No. 62/258,836, filed on Nov. 23, 2015.

(51) Int. Cl.
*A61B 18/04* (2006.01)
*A61B 18/24* (2006.01)
*A61B 18/00* (2006.01)
*A61B 18/20* (2006.01)

(52) U.S. Cl.
CPC .... *A61B 18/245* (2013.01); *A61B 2018/0041* (2013.01); *A61B 2018/00577* (2013.01); *A61B 2018/206* (2013.01)

(58) Field of Classification Search
CPC ................... A61B 18/245; A61B 2018/00577
See application file for complete search history.

(56) References Cited

U.S. PATENT DOCUMENTS

| | | | |
|---|---|---|---|
| 3,740,113 A | 6/1973 | Cass | |
| 3,995,934 A | 12/1976 | Nath | |
| 4,009,382 A | 2/1977 | Nath | |
| 4,045,119 A | 8/1977 | Eastgate | |
| 4,380,460 A | 4/1983 | Otstot et al. | |

(Continued)

FOREIGN PATENT DOCUMENTS

| | | | |
|---|---|---|---|
| CN | 1652722 A | 8/2005 | |
| CN | 1832708 A | 9/2006 | |

(Continued)

OTHER PUBLICATIONS

Invitation to Pay Additional Fees, dated Apr. 29, 2021 in International Patent Application No. PCT/US2021/019199 filed: Feb. 23, 2021.

(Continued)

*Primary Examiner* — Eric D. Bertram
(74) *Attorney, Agent, or Firm* — Schmeiser, Olsen & Watts LLP

(57) ABSTRACT

Laser ablation catheters and methods of using same for efficient tissue ablation are disclosed. In some cases, laser ablation catheter embodiments may include expanded distal tips that allow for beam energy expansion and reduce dead space at the distal cutting surface of the laser ablation catheter.

8 Claims, 11 Drawing Sheets

(56) References Cited

U.S. PATENT DOCUMENTS

| | | |
|---|---|---|
| 4,516,972 A | 5/1985 | Samson et al. |
| 4,530,569 A | 7/1985 | Squire |
| 4,641,912 A | 2/1987 | Goldenberg |
| 4,686,979 A | 8/1987 | Gruen et al. |
| 4,720,166 A | 1/1988 | Ohmori et al. |
| 4,732,448 A | 3/1988 | Goldenberg |
| 4,739,768 A | 4/1988 | Engleson |
| 4,747,405 A | 5/1988 | Leckrone |
| 4,747,662 A | 5/1988 | Fitz |
| 4,762,129 A | 8/1988 | Bonzel |
| 4,770,653 A | 9/1988 | Shturman |
| 4,784,132 A | 11/1988 | Fox et al. |
| 4,784,135 A | 11/1988 | Blum et al. |
| 4,793,359 A | 12/1988 | Sharrow |
| 4,799,754 A | 1/1989 | Goldenberg |
| 4,800,876 A | 1/1989 | Fox et al. |
| 4,834,093 A | 5/1989 | Littleford et al. |
| 4,844,062 A | 7/1989 | Wells |
| 4,848,336 A | 7/1989 | Fox et al. |
| 4,850,351 A | 7/1989 | Herman et al. |
| 4,862,886 A | 9/1989 | Clarke et al. |
| 4,907,133 A | 3/1990 | Nath |
| 4,913,142 A | 4/1990 | Kittrell et al. |
| 4,919,508 A | 4/1990 | Grace et al. |
| 4,927,231 A | 5/1990 | Levatter |
| 4,930,863 A | 6/1990 | Croitoriu et al. |
| 4,998,794 A | 3/1991 | Holzman |
| 5,005,944 A | 4/1991 | Laakmann et al. |
| 5,037,404 A | 8/1991 | Gold et al. |
| 5,040,548 A | 8/1991 | Yock |
| 5,041,108 A | 8/1991 | Fox et al. |
| 5,061,273 A | 10/1991 | Yock |
| 5,076,659 A | 12/1991 | Bekiarian et al. |
| 5,100,388 A | 3/1992 | Behl et al. |
| 5,157,750 A | 10/1992 | Grace et al. |
| 5,165,773 A | 11/1992 | Nath |
| 5,176,674 A | 1/1993 | Hofmann |
| 5,188,632 A | 2/1993 | Goldenberg |
| 5,263,952 A | 11/1993 | Grace et al. |
| 5,267,341 A | 11/1993 | Shearin |
| 5,267,993 A | 12/1993 | Grace et al. |
| 5,290,277 A | 3/1994 | Vercimak et al. |
| 5,304,171 A | 4/1994 | Gregory et al. |
| 5,321,783 A | 6/1994 | Nielson et al. |
| 5,350,395 A | 9/1994 | Yock |
| 5,374,266 A | 12/1994 | Kataoka et al. |
| 5,395,361 A | 3/1995 | Fox et al. |
| 5,412,750 A | 5/1995 | Nath |
| 5,419,760 A | 5/1995 | Narcisco, Jr. |
| 5,429,604 A | 7/1995 | Hammersmark et al. |
| 5,429,617 A | 7/1995 | Hammersmark et al. |
| 5,438,873 A | 8/1995 | Wlodarczyk et al. |
| 5,456,680 A | 10/1995 | Taylor et al. |
| 5,484,433 A | 1/1996 | Taylor et al. |
| 5,497,441 A | 3/1996 | Croitoru et al. |
| 5,514,128 A | 5/1996 | Hillsman et al. |
| 5,573,531 A | 11/1996 | Gregory |
| 5,584,558 A | 12/1996 | Nath |
| 5,675,689 A | 10/1997 | Nath |
| 5,722,972 A | 3/1998 | Power |
| 5,737,473 A | 4/1998 | Nath |
| 5,836,940 A | 11/1998 | Gregory |
| 5,857,052 A | 1/1999 | Nath |
| 5,868,665 A | 2/1999 | Biggs |
| 5,976,093 A | 11/1999 | Jang |
| 5,989,243 A | 11/1999 | Goldenberg |
| 6,022,309 A | 2/2000 | Celliers et al. |
| 6,106,510 A | 8/2000 | Lunn et al. |
| 6,117,128 A | 9/2000 | Gregory |
| 6,143,013 A | 11/2000 | Samson et al. |
| 6,163,641 A | 12/2000 | Eastgate |
| 6,165,163 A | 12/2000 | Chien et al. |
| 6,212,422 B1 | 4/2001 | Berg et al. |
| 6,263,236 B1 | 7/2001 | Kasinkas et al. |
| 6,306,124 B1 | 10/2001 | Jones et al. |
| 6,314,226 B1 | 11/2001 | Nath |
| 6,314,227 B1 | 11/2001 | Nath |
| 6,368,318 B1 | 4/2002 | Visuri et al. |
| 6,418,257 B1 | 7/2002 | Nath |
| 6,507,688 B1 | 1/2003 | Nath |
| 6,520,934 B1 | 2/2003 | Lee et al. |
| 6,571,049 B1 | 5/2003 | Nath |
| 6,585,760 B1 | 7/2003 | Fogarty |
| 6,609,014 B1 | 8/2003 | Allison et al. |
| 6,824,553 B1 | 11/2004 | Samson et al. |
| 6,893,427 B1 | 5/2005 | Jimenez |
| 6,963,688 B2 * | 11/2005 | Nath .......... G02B 6/0006 385/125 |
| 6,974,473 B2 | 12/2005 | Barclay et al. |
| 7,050,692 B2 | 5/2006 | Harlen et al. |
| 7,144,248 B2 | 12/2006 | Irwin |
| 7,144,381 B2 | 12/2006 | Gertner |
| 7,167,622 B2 | 1/2007 | Temelkuran et al. |
| 7,402,151 B2 | 7/2008 | Rosenman et al. |
| 7,572,254 B2 | 8/2009 | Herbert et al. |
| 7,762,980 B2 | 7/2010 | Gertner |
| 8,152,795 B2 | 4/2012 | Farr et al. |
| 8,231,551 B2 | 7/2012 | Griffin et al. |
| 8,652,084 B2 | 2/2014 | Akingba |
| 9,339,628 B2 | 5/2016 | Adams et al. |
| 9,700,655 B2 * | 7/2017 | Laudenslager ........ A61L 29/085 |
| 9,962,527 B2 | 5/2018 | Laudenslager et al. |
| 10,384,038 B2 | 8/2019 | Laudensalger et al. |
| 10,478,251 B2 | 11/2019 | Shuffler et al. |
| 10,485,613 B2 | 11/2019 | Hendrick et al. |
| 10,492,876 B2 | 12/2019 | Anastassiou et al. |
| 10,555,772 B2 * | 2/2020 | Laudenslager ...... A61B 18/245 |
| 10,799,671 B2 | 10/2020 | Shimada et al. |
| 2003/0023236 A1 | 1/2003 | Ashok et al. |
| 2003/0078569 A1 | 4/2003 | Caldera et al. |
| 2003/0158561 A1 | 8/2003 | Kanesaka |
| 2004/0220473 A1 | 10/2004 | Lauldi |
| 2005/0031281 A1 | 2/2005 | Nath |
| 2005/0254237 A1 | 11/2005 | Nath et al. |
| 2006/0253048 A1 | 11/2006 | Jones et al. |
| 2006/0271090 A1 | 11/2006 | Shaked et al. |
| 2007/0244495 A1 | 10/2007 | Kwon |
| 2008/0188793 A1 | 8/2008 | Kozak et al. |
| 2008/0249515 A1 | 10/2008 | Taylor |
| 2009/0112198 A1 | 4/2009 | Khanna et al. |
| 2009/0163899 A1 | 6/2009 | Burton et al. |
| 2009/0227997 A1 | 9/2009 | Wang et al. |
| 2009/0254074 A1 | 10/2009 | Splinter et al. |
| 2009/0264898 A1 | 10/2009 | Miller et al. |
| 2010/0004607 A1 | 1/2010 | Wilson et al. |
| 2010/0016842 A1 | 1/2010 | Fix |
| 2010/0087783 A1 | 4/2010 | Weber et al. |
| 2010/0114081 A1 | 5/2010 | Keeler et al. |
| 2010/0152720 A1 | 6/2010 | Sauro et al. |
| 2010/0198193 A1 | 8/2010 | Trapp |
| 2011/0238041 A1 | 9/2011 | Lim et al. |
| 2012/0277671 A1 | 11/2012 | Fuentes |
| 2013/0096545 A1 * | 4/2013 | Laudenslager ......... A61L 29/08 606/7 |
| 2015/0057639 A1 | 2/2015 | Storbeck et al. |
| 2015/0105714 A1 | 4/2015 | Laudenslager et al. |
| 2017/0143424 A1 | 5/2017 | Laudenslager et al. |
| 2017/0266351 A1 | 9/2017 | Laudenslager et al. |
| 2018/0008348 A1 | 1/2018 | Grace et al. |
| 2018/0021550 A1 | 1/2018 | Laudenslager et al. |
| 2018/0021551 A1 | 1/2018 | Laudenslager et al. |
| 2018/0021552 A1 | 1/2018 | Laudenslager et al. |
| 2018/0250498 A1 | 9/2018 | Stern et al. |
| 2019/0142517 A1 | 5/2019 | Chia et al. |
| 2019/0160259 A1 | 5/2019 | Cottone et al. |
| 2019/0290356 A1 | 9/2019 | Wood et al. |
| 2019/0366036 A1 | 12/2019 | Jalgaonkar et al. |
| 2020/0046429 A1 | 2/2020 | Tschida et al. |

(56) References Cited

U.S. PATENT DOCUMENTS

2020/0230294 A1    7/2020  Laudenslager et al.
2020/0261154 A1    8/2020  Ogata et al.

FOREIGN PATENT DOCUMENTS

| EP | 0247746 | 12/1987 |
|---|---|---|
| EP | 0368512 | 5/1990 |
| EP | 0590268 | 4/1994 |
| EP | 0727054 | 8/1996 |
| EP | 1757428 | 2/2007 |
| EP | 2301617 | 3/2011 |
| WO | WO 95/012138 | 5/1995 |
| WO | WO 97/039691 | 10/1997 |
| WO | WO 98/038538 | 9/1998 |
| WO | WO 00/030696 | 6/2000 |
| WO | WO 09/120871 | 10/2009 |

OTHER PUBLICATIONS

Notice of Allowance dated Jun. 17, 2021 in U.S. Appl. No. 16/359,889, filed Mar. 20, 2019.
"Prevalence and Cost of ESRD Therapy," USRDS Annual Data Report 1991, American Journal of Kidney Diseases, vol. 18, No. 3, Suppl 2, Nov. 1991; pp. 21-29.
Bittl; Catheter Interventions for Hemodiaylysis Fistula and Grafts: J Am Coll Cardiol Intv vol. 3 pp. 1-11 (2010).
Das, "Excimer Laser-Assisted Angioplasty for Infrainguinal Artery Disease" J of Endovasc Therapy vol. 16 pp. 1198-11104(2009).
Drooz, "Ultrahigh-pressure angioplasty of a transposed brachiocephalic fistula with recurrent stenosis," ConQuest PTA Dilation Catheter, Bard Peripheral Vascular, Innova Fairfax Hospital; Fairfax Hospital, Aug. 2005.
Forauer, Hoffer, et al.; "Dialysis Access Venous Stenoses: Treatment with Balloon Angioplasty-1- versus 3-minute Inflation Times" Radiology vol. 249, pp. 375-381 (2008).
Gandini and Del Giudice; "Use of laser Atherectomy with drug-eluting balloon angioplasty shows benefit in treatment of in-stent restenosis" presented at EuroPCR 2014 Congress (May 20-23, 2014).
Haage, Verwerk et al.:" Percutaneous treatment of thrombosed primary arteriovenous hemodialysis access fistulae" Kidney International, vol. 57, pp. 1169-1175(2000).
Hamburger et al., New Aspects of Excimer Laser Coronary Angioplasty Physical Aspects and Clinical Results, printed by Optima Grafische Communicatie ISBN 90-73235-27-8, Rotterdam, Jaap N. Hamburger, Dec. 1998.
Hofstra et al., "Enhanced Cellular Proliferation in Intact Stenotic Lesions Derived From Human Arteriovenous Fistulas and peripheral Bypass Grafts. Does it correlate with Flow Parameters?" Circulation, 1996;94:1283-1290.
Janis et al. "Laser Thrombolysis in an in vitro Model" Lasers in Surg.: Advanced Characterization, Therapeutics and Systems, Pro. of SPIE vol. 3907 pp. 582-585 (2000).
Ma et al., "Interaction of excimer laser with blood components and thrombosis" Life Science J. vol. 5 pp. 19-26 (2008).
Mickley; "Stenosis and thrombus in hemodialysis fistula and grafts: the surgeon's point of view" Nephrol Dial Transplant vol. 19 pp. 309-311 (2001).
Miller and Friedman, "Balloon-Assisted Maturation of Arteriovenous Fistulas" Endovascular Today Endovascular Today, pp. 46-54 (2010).
Morph ® "Universal Deflectable Guide Catheder," BioCardia® Cat # 01037-5.
Mysliwiec, "Vascular access thrombosis-what are the possibilities of intervention?" Nephrol Dial Transplant (1997) 12: Editorial Comments.
Ozkan, Gungor et al. "Endovascular Stent Placement of Juxtaanastomotic Stenosis in Native Arteriovenus Fistula After Unsuccessful Balloon Angioplasty" Iranian J of Radiology, vol. 10 pp. 133-139 (2013).
Papaioannou et al. "Excimer Laser Assisted Thrombolysis: The Effect of Fluence, Repetition Rate and Catheter Size" Proc. SPIE 4609, Lasers in Surgery; Advanced Characterization, Therapeutics and Systems XII 413 (2002).
Papaioannou et al. "Particulate debris analysis during excimer laser thrombolysis: An in-vitro study" Proc. SPIE 4609, Lasers in Surgery; Advanced Characterization, Therapeutics and Systems XII 404 (2002).
Shenoy, "Surgical anatomy of upper arm: what is needed for AVF planning" J of Vascul Access vol. 10 pp. 223-232(2009).
Sofocleous et al.;"Dialysis Fistulas" In Medscape (2013).
Staniloae et al. "Obrital Atherectomy: Device Evolution and Clinical Data" Periperal Vase. Disease, vol. 26,pp. 215-219 (2014).
Van den Berg, Pedrotti et al.; "In-Stent Restenosis: Mid-Term Results of Debulking Using Excimer Laser and Drug-Eluting Balloons: Sustained Benefit?" J Invasive Cardiol vol. 26 pp. 333-337(2014).
Van den Berg; " Atherectomy and DCB in the SFA: A Summary of the Data" Endovascular Today pp. 28-32(2014).
Walker et al., "Excimer Laser-Assisted Angioplasty" Endovasc. Today,pp. 75-76 (2007).
Zaleski; "Declotting, Maintenance, and Avoiding Procedural Complications of Native Arteriovenus Fistulae" Semin Intervent Radiol. vol. 21, pp. 83-93 (2004).
Zwaan et al., "Initial clinical experience with a new pulsed dye laser device in angioplasty of limb ischemia and shunt fistula obstructions," European Journal of Radiology, 14 (1992) pp. 72-76.
Extended European Search Report dated May 29, 2015 in European Patent Application No. EP 12840010.8, filed: Oct. 12, 2012.
International Preliminary Report on Patentability dated Apr. 24, 2014 in International Application No. PCT/US2012/060065 filed Oct. 12, 2012.
International Search Report and Written Opinion dated Mar. 29, 2013 in International Application No. PCT/US2012/060065 filed Oct. 12, 2012.
Notice of Allowance dated Apr. 20, 2017 in U.S. Appl. No. 13/651,070, filed Oct. 12, 2012 and published as: US-2013/0096545 on: Apr. 18, 2013 and issued as: 9,700,655 on Jul. 11, 2017.
Final Office Action dated Sep. 15, 2016 in U.S. Appl. No. 13/651,070, filed Oct. 12, 2012 and published as: US-2013/0096545 on: Apr. 18, 2013 and issued as: 9,700,655 on Jul. 11, 2017.
Non-Final Office Action dated Feb. 12, 2016 in U.S. Appl. No. 13/651,070, filed Oct. 12, 2012 and published as: US-2013/0096545 on: Apr. 18, 2013 and issued as: U.S. Pat. No. 9,700,655 on Jul. 11, 2017.
Notice of Allowance dated Jan. 30, 2018 in U.S. Appl. No. 14/515,435, filed Oct. 15, 2014, published as: 2015/0105714 on Apr. 16, 2015 and issued as: U.S. Pat. No. 9,962,527 on May 8, 2018.
ExParte Quayle Action dated Dec. 12, 2017 in U.S. Appl. No. 14/515,435, filed Oct. 15, 2014, published as: 2015/0105714 on Apr. 16, 2015 and issued as: U.S. Pat. No. 9,962,527 on May 8, 2018.
Notice of Allowance dated Apr. 19, 2019 in U.S. Appl. No. 15/723,062, filed Oct. 2, 2017, published as: 2018/0021551 on Jan. 25, 2018.
Non Final Office Action dated Dec. 31, 2018 in U.S. Appl. No. 15/723,062, filed Oct. 2, 2017, published as: 2018/0021551 on Jan. 25, 2018.
Non Final Office Action dated Nov. 30, 2018 in U.S. Appl. No. 15/723,057, filed Oct. 2, 2017, published as: 2018/0021550 on Jan. 25, 2018 and issued as: U.S. Pat. No. 10,245,417 on Apr. 2, 2019.
Notice of Allowance dated Dec. 31, 2018 in U.S. Appl. No. 15/723,057, filed Oct. 2, 2017, published as: 2018/0021550 on Jan. 25, 2018 and issued as: U.S. Pat. No. 10,245,417 on Apr. 2, 2019.
Notice of Allowance dated Feb. 26, 2019 in U.S. Appl. No. 15/723,057, filed Oct. 2, 2017, published as: 2018/0021550 on Jan. 25, 2018 and issued as: U.S. Pat. No. 10,245,417 on Apr. 2, 2019.
Notice of Allowance dated Apr. 17, 2019 in U.S. Appl. No. 15/723,067, filed Oct. 2, 2017, published as: 2018/0021552 on Jan. 25, 2018.
Notice of Allowance dated Feb. 27, 2019 in U.S. Appl. No. 15/723,067, filed Oct. 2, 2017, published as: 2018/0021552 on Jan. 25, 2018.

(56) References Cited

OTHER PUBLICATIONS

ExParte Quayle Action dated Nov. 29, 2018 in U.S. Appl. No. 15/723,067, filed Oct. 2, 2017, published as: 2018/0021552 on Jan. 25, 2018.

Extended European Search Report dated Aug. 13, 2019 in European Patent Application No. EP 19163464.1, filed: Mar. 18, 2019.

Notice of Allowance dated Oct. 17, 2019 in U.S. Appl. No. 15/359,412, filed Nov. 22, 2016, published as: 2017/0143424 on May 25, 2017.

Non-Final Office Action dated Aug. 5, 2019 in U.S. Appl. No. 15/359,412, filed Nov. 22, 2016, published as: 2017/0143424 on May 25, 2017.

Non-Final Office Action dated Jan. 9, 2020 in U.S. Appl. No. 15/987,838, filed May 23, 2018, published as: 2018/0339136 on Nov. 29, 2018.

Non-Final Office Action dated Jan. 12, 2021 in U.S. Appl. No. 16/359,889, filed Mar. 20, 2019 and published as: US-2019/0290356 on: Sep. 26, 2019.

Non-Final Office Action dated Apr. 1, 2021 U.S. Appl. No. 16/549,516, filed Aug. 23, 2019 and published as: US-2019/0374684 on: Dec. 12, 2019.

Non-Final Office Action dated Sep. 9, 2020 in U.S. Appl. No. 15/615,734, filed Jun. 6, 2017 and published as: US-2017/0266351 on: Sep. 21, 2017.

Non-Final Office Action dated Sep. 30, 2020 in U.S. Appl. No. 16/502,766, filed Jul. 3, 2019 and published as: US-2019/0336732 on: Nov. 7, 2019.

International Search Report and Written Opinion dated Jul. 12, 2021 in International Patent Application: PCT/US21/19199 filed Feb. 23, 2021.

Non-Final Office Action dated Oct. 13, 2021 in U.S. Appl. No. 16/843,736, filed Apr. 8, 2020 and published as: 2020/0230294 on Jul. 23, 2020.

\* cited by examiner

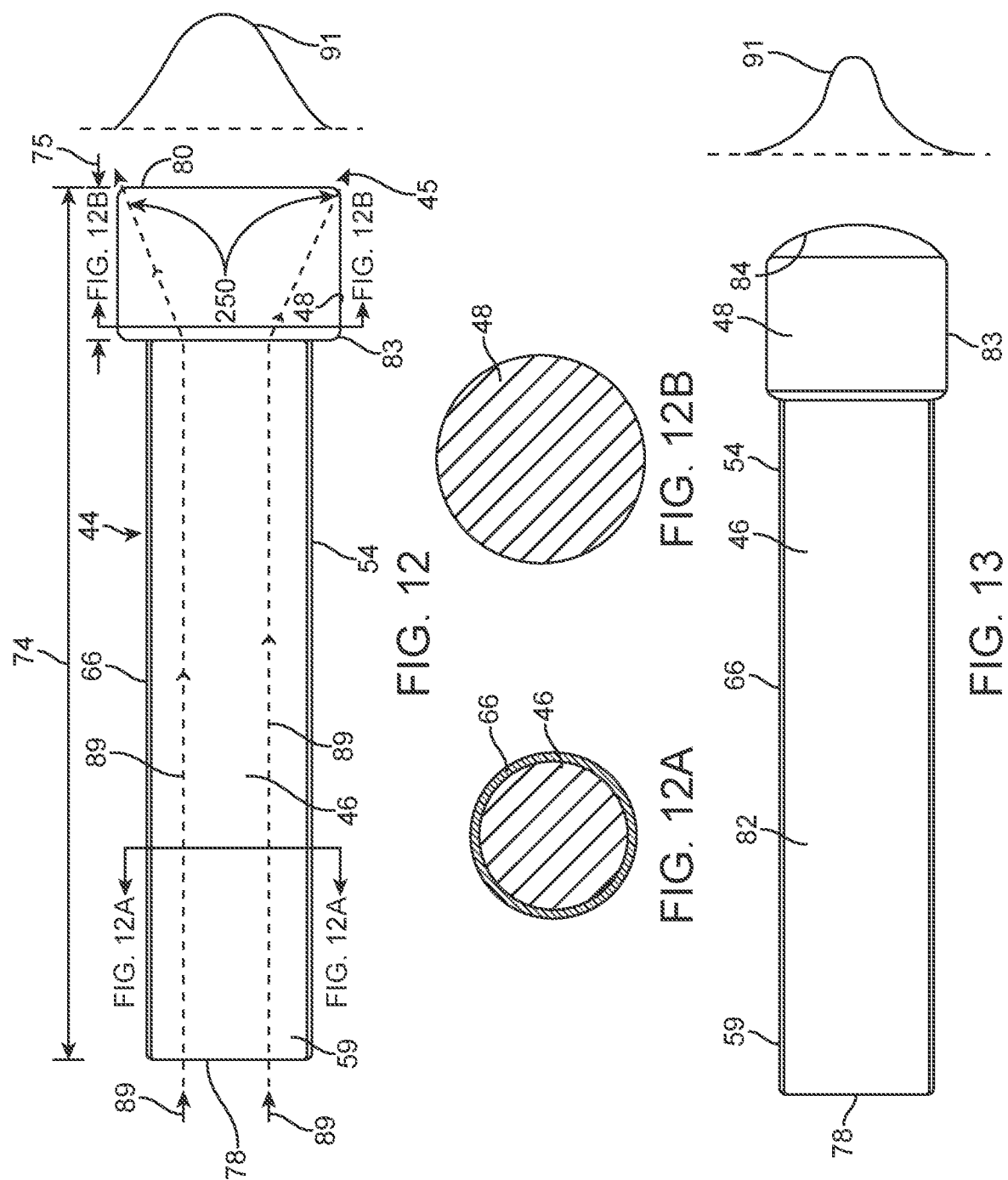

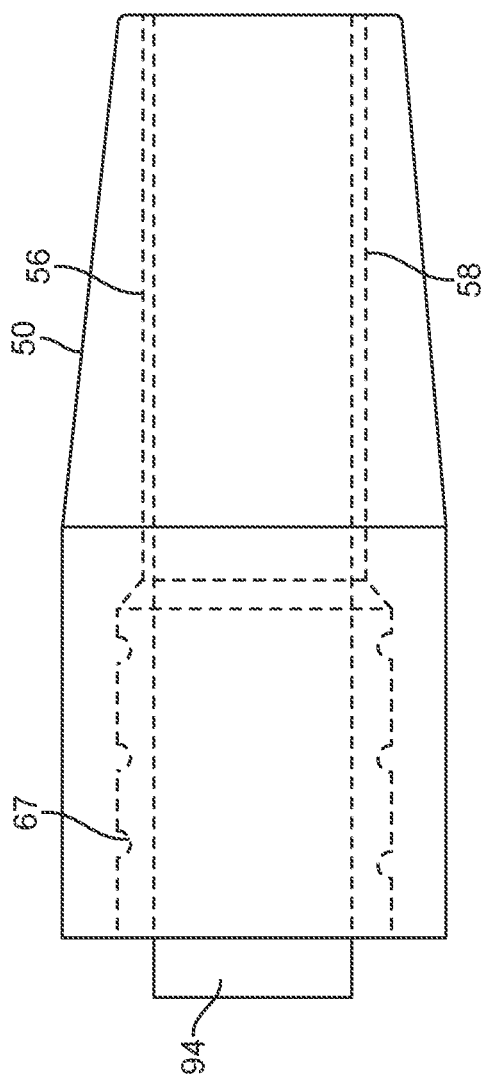
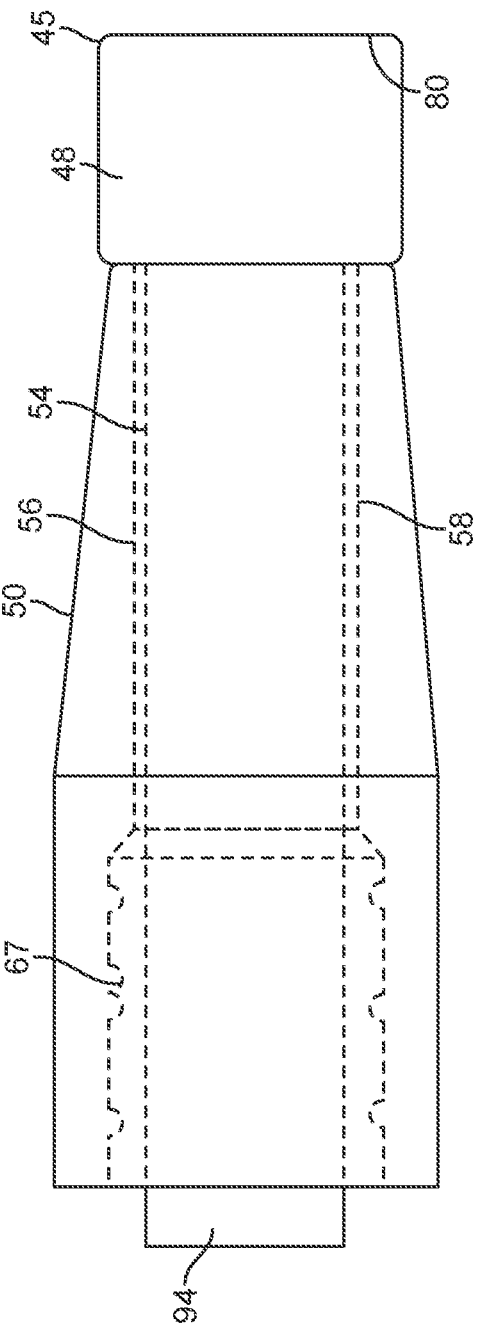

LASER ABLATION CATHETERS HAVING EXPANDED DISTAL TIP WINDOWS FOR EFFICIENT TISSUE ABLATION

RELATED APPLICATIONS

This application is a continuation of copending U.S. patent application Ser. No. 15/359,412, now U.S. Pat. No. 10,555,772, filed Nov. 22, 2016, entitled LASER ABLATION CATHETERS HAVING EXPANDED DISTAL TIP WINDOWS FOR EFFICIENT TISSUE ABLATION, by J. Laudenslager et al., which claims priority under 35 U.S.C. Section 119(e) from U.S. Provisional Patent Application Ser. No. 62/258,836, filed Nov. 23, 2015, by J. Laudenslager et al., titled ENLARGED SHAPED DISTAL WINDOW TIPS FOR LASER ABLATION CATHETERS, each of which is incorporated by reference herein in its entirety.

BACKGROUND

Some pulsed laser energy transmitting catheters currently used for ablating and clearing blockages in human arteries may use a single large diameter fiber optic which tends to be stiff for some such indications. For improved catheter flexibility, multiple smaller diameter fiber optics may be used which are arranged in various shaped bundles. In some cases, excimer laser ablation efficiency of atheroma may be inversely proportional to the relative amount of inactive surface area or dead space at the ablation catheter tip contacting the target surface being ablated. Multiple fiber optic based catheters may have a significant amount of dead space, which may be due to the cladding, buffer, fiber packing factor, glue and the sidewall of the catheter outside tubing along with a guidewire lumen tubing or the like.

A doctoral thesis by Hamburger showed ablation histology for multiple fiber optic bundle ablation catheters versus a single fiber optic and indicated that the dead space leads to more tissue damage and less efficient ablation than a window tip with a homogonous energy distribution ablating surface, "New Aspects of Excimer Laser Coronary Angioplasty Physical Aspects and Clinical Results, printed by Optima Grafische Communicatie ISBN 90-73235-27-8, Rotterdam, Jaap N. Hamburger, 1999. Hamburger's conclusions stated that: "Optimization of excimer laser coronary angioplasty can be achieved by elimination of ultraviolet-absorbing media, reduction of catheter advancement speeds and by reduction of the non-light emitting area at the tip of a laser catheter." What are needed are catheter device configurations and methods for use thereof which allow for increased optical beam expansion of the optical beam which exits the distal portion of the catheter and which reduce dead space due to catheter elements which encompass an optical window at a distal portion of a laser catheter.

SUMMARY

Some embodiments of a laser ablation catheter to ablate blockages in body lumens using high energy and high power laser pulses include a liquid filled waveguide. The liquid filled waveguide may include an elongate catheter body tube having an inner surface with a first index of refraction and a biocompatible ultraviolet transparent optical fluid disposed within and completely filling a core liquid volume of the elongate catheter body tube which is at least partially bounded by the inner surface, with the optical fluid having a second index of refraction which is greater than the first index of refraction. The laser ablation catheter may also include an ultraviolet grade elongated distal optical window disposed in liquid sealed relation to a surface of the elongate catheter body tube at a distal end of the elongate catheter body tube. The distal optical window may further have an insert segment which is disposed within a distal section of the elongate catheter body tube and which includes a core and cladding configured to act as a waveguide. The distal optical window may also have an expanded segment which is disposed distally of the insert segment, which does not have a core and cladding configured to act as a waveguide, which has an outer diameter which is greater than an outer diameter of the insert segment, which has an output surface that has an area which is equal to or greater than an area of a transverse section of the elongate catheter body tube proximally adjacent the distal optical window and which has an axial length sufficient to allow optical energy expansion within the expanded segment such that a optical energy emitted from the output surface produces a hole in target tissue having a diameter equal to or greater than an outer diameter of the elongate catheter body tube proximally adjacent the distal optical window.

Some embodiments of a laser ablation catheter to ablate blockages in body lumens using high energy laser pulses with a pulse duration of less than 100 nanoseconds may include a liquid filled waveguide including an elongate catheter body tube having an inner surface with a first index of refraction and a biocompatible ultraviolet transparent optical fluid disposed within and completely filling an inner lumen of the elongate catheter body tube, with the optical fluid having a second index of refraction which is greater than the first index of refraction. Such laser ablation catheters may also include an ultraviolet grade elongated distal optical window disposed in liquid sealed relation to a surface of the elongate catheter body tube at a distal end of the elongate catheter body tube. The distal optical window may further have an insert segment which is disposed within a distal section of the elongate catheter body tube and which comprises an ultraviolet grade material. A layer of material may be disposed about an outer surface of the insert segment which includes an index of refraction lower than an index of refraction of the material of the insert segment or a reflective material. In addition, the distal optical window may further include an expanded segment which is disposed distally of the insert segment, which is not configured to act as a waveguide, which has an outer diameter which is greater than an outer diameter of the insert segment, which has an output surface that has an area which is equal to or greater than an area of a transverse section of the elongate catheter body tube proximally adjacent the distal optical window and which has an axial length sufficient to allow optical energy expansion within the expanded segment such that optical energy emitted from the output surface ablates a hole in target tissue having a diameter equal to or greater than an outer diameter of the elongate catheter body tube proximally adjacent the distal optical window.

Some embodiments of a laser ablation catheter to ablate blockages in body lumens may include a liquid filled waveguide including an elongate catheter body tube having an inner layer with a first index of refraction and a biocompatible ultraviolet transparent optical fluid disposed within and completely filling a core liquid volume of the elongate catheter body tube, with the optical fluid having a second index of refraction which is greater than the first index of refraction. The laser ablation catheter may also include a distal optical window disposed in liquid sealed relation to the elongate catheter body tube at a distal end of the elongate catheter body tube. The distal optical window may further have an insert segment which is disposed within a distal section of the catheter body tube and which includes a core and cladding configured to act as a waveguide. An expanded segment may be disposed distally of the insert segment which is not configured to act as a waveguide, which has an outer diameter which is greater than an outer diameter of the insert segment, which has an output surface that has an area which is equal to or greater than an area of a transverse section of the elongate catheter body tube proximally adjacent the distal optical window and which has an axial length sufficient to allow optical energy expansion within the expanded segment such that optical energy emitted from the output surface produces a hole in target tissue having a diameter equal to or greater than an outer diameter of the elongate catheter body tube proximally adjacent the distal optical window.

Certain embodiments are described further in the following description, examples, claims and drawings. These features of embodiments will become more apparent from the following detailed description when taken in conjunction with the accompanying exemplary drawings.

BRIEF DESCRIPTION OF THE DRAWINGS

FIG. 12 is an elevation view of an optical window embodiment having an insert segment, an expanded segment, and a substantially flat output surface.

FIG. 12A is a transverse section view of the proximal insert segment of the optical window embodiment of FIG. 12 which shows a fiber core and cladding configuration.

FIG. 12B is a transverse section view of the expanded segment of the optical window embodiment of FIG. 12 without any cladding layer.

FIG. 13 is an elevation view of an optical window embodiment having an insert segment, an expanded segment, and a substantially convex output surface with rounded edges.

FIG. 16 is an elevation view of the tapered window housing embodiment of FIG. 15 and an optical window embodiment having a constant diameter disposed within and secured to the tapered window housing.

FIG. 17 is an elevation view of the tapered window housing embodiment of FIG. 15 and an optical window embodiment having an insert segment and an expanded segment disposed within and secured to the tapered window housing.

Figure 1:
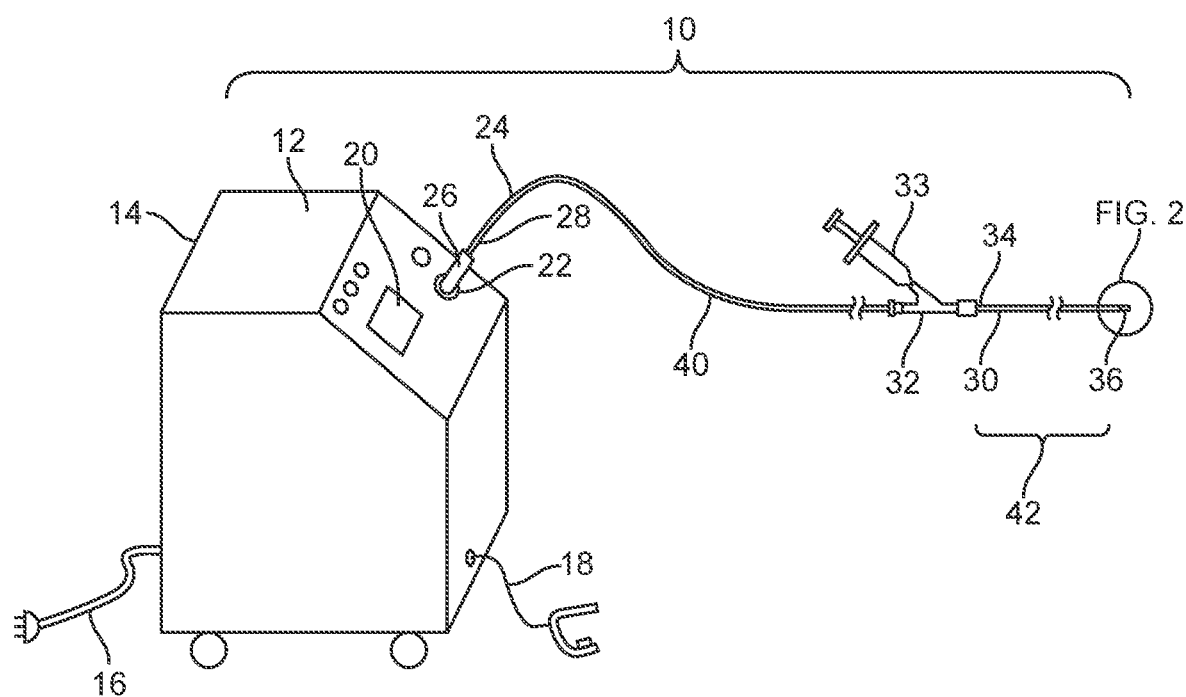
FIG. 1 is a perspective view of a laser system embodiment including a laser and a disposable liquid core laser ablation catheter coupled to the laser.

The drawings illustrate embodiments of the technology and are not limiting. For clarity and ease of illustration, the drawings may not be made to scale and, in some instances, various aspects may be shown exaggerated or enlarged to facilitate an understanding of particular embodiments.

DETAILED DESCRIPTION

Laser ablation catheters and laser delivery systems in general have a wide range of applications in the medical field. Such systems may be used to deliver laser energy to desired sites of a patient's anatomy, and may be particularly suitable for delivering laser energy to locations inside a patient's body that allow for minimally invasive treatment of a variety of indications using a variety of treatment modalities. Example of some treatment modalities include, heating tissue, stimulating tissue, drug activation within a patient's tissue and ablation of tissue or other organic or calcium materials within a patient. Some examples of clinical indications for laser treatment may include laser atherectomy and the use of a laser catheter to cross total or partial occlusions of body vessels.

One drawback of some current laser systems is the cost of the systems and devices used to deliver the laser energy, particularly those components that are designated as single use products. Liquid core laser ablation catheter embodiments may generally be considerably less expensive than a silica fiber optic based laser catheter and may also have less dead space at the ablation tip for contact cutting. Liquid filled ablation catheters may eliminate most of the dead space inside a catheter body tube compared to multiple fiber optic bundles but may still have residual dead space, which consists of the distal fiber window cladding and the outside wall of the metal tip or catheter tube that holds the window. Using a tapered metal tip, as disclosed for a liquid filled catheter in co-owned patent application number U.S. patent application Ser. No. 13/651,070, Publication No. 2013/0096545, filed by J. Laudenslager et al., on Oct. 12, 2012, titled Small Flexible Liquid Core Catheter for Laser Ablation in Body Lumens and Methods for Use, which is hereby incorporated by reference herein in its entirety, minimizes the initial dead space. For example, a 5 French liquid filled ablation catheter with a tapered metal tip may have a 70 percent active area at the tip that gradually reduces to 42 percent once the catheter tip penetrates the target past the tapered metal sheath. Multiple fiber optic based catheters, ignoring the guide wire lumen, may have about 17 percent to 30 percent active cutting area in some cases depending on the design at the tip. Multiple fiber optic based catheters may need to be operated at higher energy fluences and repetition rates compared to fluences and repetition rates of single fiber optic systems or the like in order to cut as efficiently as a laser ablation catheter having a homogenous laser energy output at the output surface of the distal optical window.

Liquid core laser ablation catheters discussed herein have less dead space and needs less energy density to ablate tissue compared generally to multiple fiber optic laser ablation catheter designs currently in commercial use. The reduced dead space (that distal surface area that is not emitting laser energy) may be an important feature for ablation of blockages in arteries and for the ability of the laser ablation catheter to cross a lesion in a patient's vessel. Some embodiments of liquid core laser ablation catheters may incorporate an optical window having an expanded segment with a stepped configuration which is configured to increase the output surface of the liquid core laser ablation catheter, minimize the dead space of the liquid core laser ablation catheter, and allow for easier passage of the liquid core laser ablation catheter through tight lesions which are disposed within the vasculature of a patient with less pulse energy needed.

Some embodiments of a laser ablation system may include a laser energy source and a liquid core laser ablation catheter. Some embodiments of the system may also include a laser coupler which is disposed at a proximal section of the liquid core laser ablation catheter. The liquid core laser ablation catheter may include a working length section which is disposed between the proximal section and a distal section of the liquid core laser ablation catheter. The working length section of the liquid core laser ablation catheter may include a catheter body tube which may feature an inner lumen which is disposed within the catheter body tube.

In some cases, the inner lumen may be coated with an optical coating, with the optical coating spanning the working length section. An optical fluid may be disposed within a core liquid volume at least partially bounded by the inner lumen of the catheter body tube, with the optical fluid being in optical communication with the laser coupler. The distal section of the liquid core laser ablation catheter may include a window housing having a tubing cavity which may be secured to the catheter body tube. An optical window may be partially disposed within and secured to the window housing, in optical communication with the optical fluid.

Some embodiments of the distal optical window may include an expanded segment which has an outer radial surface that extends radially beyond an outer radial surface of an insert segment of the optical window, with an outer surface of the insert segment being configured to couple to an interior window surface of the window housing. The expanded segment may extend distally beyond a distal portion and/or distal end of the window housing. In some cases, the outer diameter of the expanded segment may be equal to or greater than an outer diameter of the window housing, thereby allowing optical energy which exits the optical window through an output surface of the expanded segment to ablate a surface area of target material which is greater than or equal to the surface area of the distal section of the liquid core laser ablation catheter. In some cases the optical window which includes the insert segment and the expanded segment may be formed from a single length of ultraviolet grade silica over silica core-clad fiber optic.

Some liquid core laser ablation catheter embodiments may be configured such that optical energy may be transmitted from the laser energy source through the laser coupler, through the optical fluid which disposed within the core liquid volume in the inner lumen of the catheter body tube, through the optical window where it exits the output surface of the expanded segment, and into target tissue and/or target material which is to be ablated by the optical energy. In some cases the laser energy source may be configured as an ultraviolet laser and the optical energy may be configured as pulsed ultraviolet energy, with each ultraviolet energy pulse having sufficient pulse energy to ablate blockages in body lumens at the distal tip of the liquid core laser ablation catheter when it is curved around typical bends in a patient's vascular system. Some laser energy sources may be configured as an XeCl excimer laser with a wavelength around 308 nm, with a pulse duration greater than about 10 nanoseconds (nsec), a pulse energy fluence greater than about 6 milli-Joules per millimeter squared ($mJ/mm^2$) delivered to the distal tip of the liquid core laser ablation catheter and a repetition rate range of about 10 Hertz (Hz) to about 100 Hz. In some cases, such laser energy sources may be operated with pulse durations less than about 300 nsec, more specifically, less than about 100 nsec.

Some distal optical window embodiments may be formed monolithically from a single uninterrupted piece of feed fiber optic which is made of ultraviolet grade silica over silica which form a core and cladding of the feed fiber optic. The expanded segment of the optical window may be formed by melting a portion of the core-cladding materials of the feed fiber optic into a melted portion and forming the expanded segment from the melted portion. The portion of the feed fiber optic which has not been melted may include the insert portion of the optical window. In some cases, within the expanded segment of the optical window the cladding material may be mixed with the core material resulting in an expanded segment of the distal optical window that has no cladding or waveguide configuration, nor does it have any dead space. An outer diameter of the expanded segment may be larger than an outer radial diameter of the insert segment, and the diameter of the expanded segment may be greater than or equal to diameters of the tip or distal edge of the window housing and/or the catheter body tube proximally adjacent the distal optical window which may have a stepped configuration in some cases.

For some embodiments of distal optical windows (which may typically serve as output optical windows), the axial length of the expanded segment may be configured to be long enough to allow for an optical beam to expand to an outer diameter of the output surface of the expanded segment. The length of the expanded segment may also be configured to be axially short enough to allow for passage through tortuous pathways within a human patient's anatomical lumen. For some embodiments of such a distal optical window, the overall length of the optical window may be from about 4 millimeters (mm) to about 8 mm. For some embodiments of the optical window, the axial length of the expanded segment may be from about 0.5 mm to about 2 mm, more specifically, about 1 mm to about 2 mm in some cases. For some embodiments, the axial length of the expanded segment 48 may be 0.9 mm to 1.1 mm. The ratio of the diameter of the expanded segment to the diameter of the insert segment may be about from about 1.1:1 to about 1.5:1 in some cases.

Some or all of the edges of any distal optical window embodiments discussed herein may be filleted, rounded or chamfered in order to minimize damage or chipping during assembly, and to prevent trauma to adjacent tissue when disposed within a body lumen. For some optical window embodiments, the expanded segment and the insert segment of the optical window may be monolithically formed from sapphire window material or substrate including a feed fiber optic substrate. Some embodiments of optical windows having an expanded segment and an insert segment may be formed monolithically from a single piece of material, while other embodiments of optical windows having an expanded segment and an insert segment may be formed by welding or fusing different pieces of material together.

FIG. 1 shows a laser ablation system embodiment 10 that includes a laser energy source 12 having a housing 14, a power cord 16, an activation footswitch 18, a control panel 20 and an output coupler 22. A liquid core laser ablation catheter 24 may include a laser coupler 26 which is disposed at a proximal section 28 of the ablation catheter 24 and which may be coupled to the output coupler 22 of the laser source 12 as shown. The ablation catheter 24 may be disposed within an inner lumen of a support catheter 30 which may be used to guide or support the liquid core laser ablation catheter 24 within a body lumen of a patient. The support catheter 30 may include a Y-adapter 32 which is coupled to the proximal end 34 of the support catheter 30. The liquid core laser ablation catheter 24 may be disposed within and pass through a central lumen (not shown) of the Y-adapter 32, and a syringe 33 which may contain a normal saline solution that may be used to flush blood and contrast fluid from a distal window 80 of the ablation catheter 24 during ablation procedures. The support catheter 30 may also incorporate a radiopaque marker 36 which is disposed at a distal section 38 of the support catheter 30, the radiopaque marker 36 facilitating the visualization of the support catheter 30 when viewed under fluoroscopy.

A working length 42 of the liquid core laser ablation catheter 24 may include the length inside the patient's body between the access point and the target tissue lesion site and the length outside the patient's body necessary to couple or pass through the Y-adapter. An additional length may be needed to couple the working length 42 of 50 centimeters (cm) to 120 cm to the laser source 12 in some cases. If a laser source 12 is large and located away from the patient, an additional working length 42 may be necessary. Some liquid core laser ablation catheter embodiments 24 may be from about 2 meters to about 3 meters long in some cases.

In some cases, the laser source 12 of the laser system 10 may include a XeCl excimer laser which produces high energy pulses at a wavelength of about 308 nm, for example, 307 nm to 309 nm, however, other high energy pulsed ultraviolet laser sources may be used. Some laser source embodiments 12 may have a pulse duration of less than about 100 nsec and a repetition rate of up to about 100 Hz. Some such laser source embodiments 12 may be capable of producing about 20 milli-Joules per pulse (mJ/pulse) to about 100 mJ/pulse. For some embodiments, the transmission of laser optical energy through the liquid core laser ablation catheter with solid windows may be high enough to enable a relatively small laser source 12 to be used for the laser ablation system 10 in order to save cost and valuable catheter lab space. In contrast some previous embodiments of ablation catheters having multiple fibers may have considerable dead space at the input laser coupler, which requires a certain energy density over a larger area and hence requires higher laser optical energy output and a larger more expensive laser source 12 to achieve ablation of the target atheroma. In addition, the large dead space at the distal end of such ablation catheters having multiple fibers may require a higher energy fluence in order to overcome the dead space for efficient ablation of atheroma.

Figure 2:
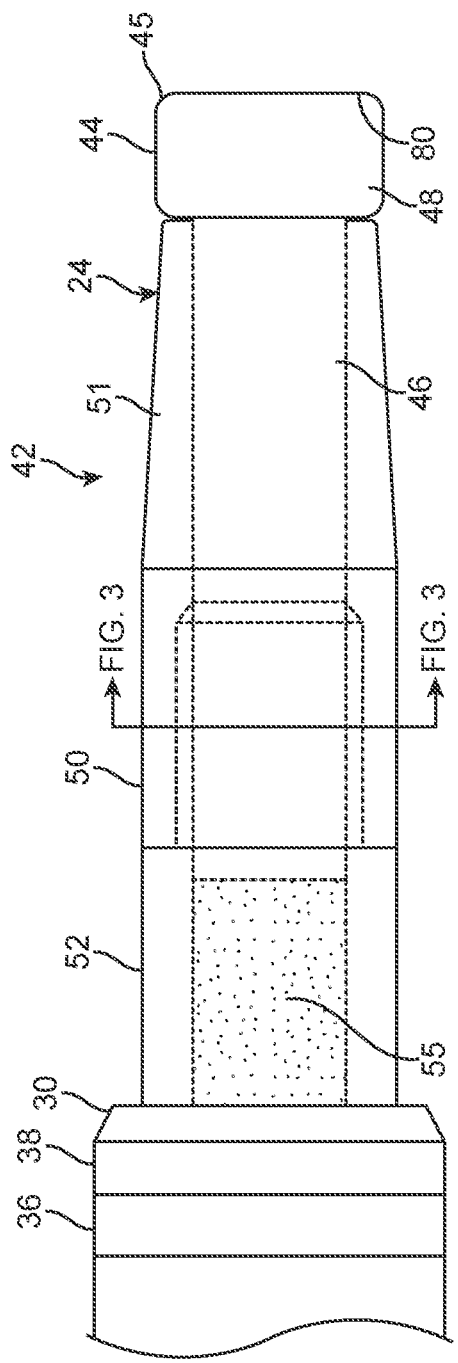
FIG. 2 is an elevation view of a distal section of a liquid core laser ablation catheter embodiment including a tapered window housing which incorporates an optical window having an expanded segment with a substantially flat output surface.

FIG. 2 is an enlarged view of the distal section 42 of the liquid core laser ablation catheter 24 which is depicted in FIG. 1, and of the distal section 38 and radiopaque marker 36 of the support catheter 30. The distal section 60 of the liquid core laser ablation catheter 24 may include a distal optical window 44 (see FIG. 12) having an insert segment 46 and an expanded segment 48. The distal optical window 44 may be partially disposed within a window housing 50 (see FIG. 15), the window housing 50 may in turn be secured to a catheter body tube 52. The catheter body tube 52 may be fabricated from any suitable polymer material. In some cases, the catheter body tube may be extruded from a fluorinated ethylene propylene (FEP) fluoropolymer material. For some embodiments, the wall of the catheter body tube may incorporate a braided material or layer 57 (see FIG. 10) which may be disposed within or otherwise encapsulated by the wall material of the catheter body tube 52. The braided material may facilitate the torqueablilty and the pushability of the working length 42 of the liquid core laser ablation catheter 24.

Figure 2A:
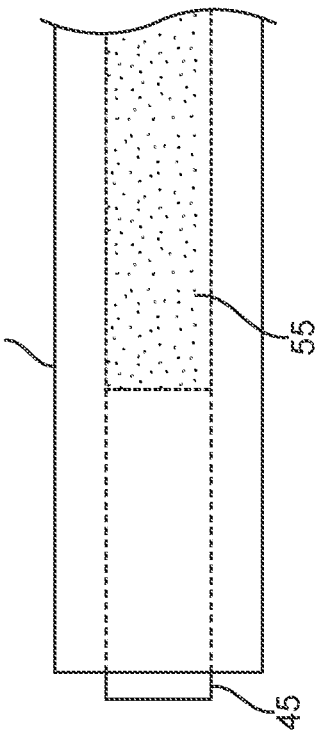
FIG. 2A is an elevation view of a proximal end of the liquid core laser ablation catheter of FIG. 2.
Figure 4:
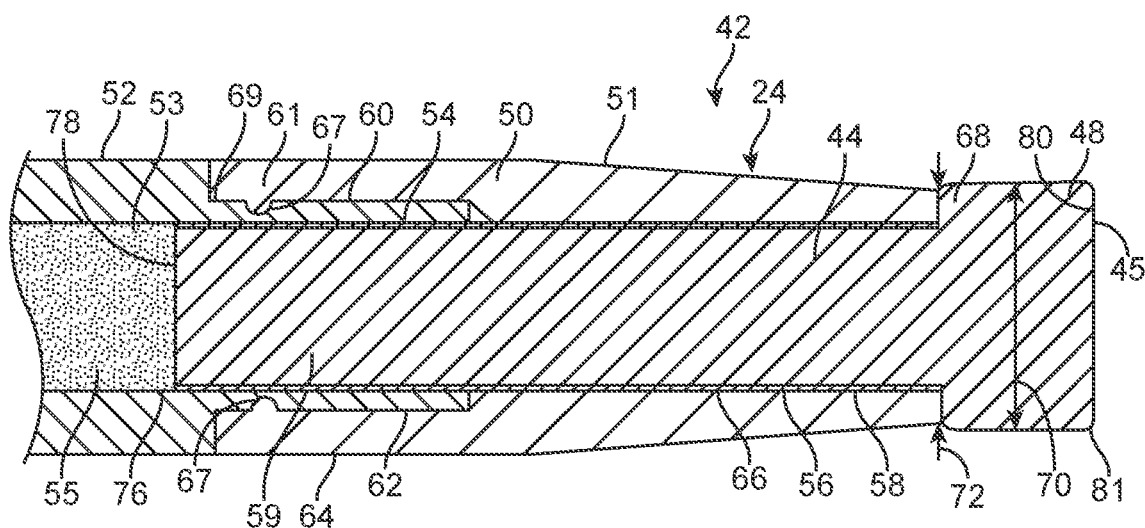
FIG. 4 is a longitudinal section view of the distal section of the liquid core laser ablation catheter embodiment of FIG. 2 which includes a distal optical window embodiment having an insert segment and an expanded segment, a tapered window housing, a catheter body tube, and an optical fluid disposed within the catheter body tube.

Some embodiments of the window housing 50 may include a tapered section 51 as shown in FIG. 2 wherein an outer profile of the window housing 50 is suitably tapered towards the distal end of the window housing 50. The window housing 50 may be formed from any suitable high strength polymer or metal material. For some embodiments, the window housing 50 may be fabricated from stainless steel, titanium or other suitable metal that may optionally serve as a radiopaque marker that may be visualized by imaging systems such as a fluoroscopy system. An interior lumen 53 of the catheter body tube as shown in FIG. 4 may contain an optical fluid 55, with the optical fluid having an index of refraction (IR) which may depend on the wavelength of the optical energy which is transmitted through the optical fluid 55. For some embodiments the IR of the optical fluid 55 may be about 1.35 to about 1.38 for optical energy which is transmitted at a wavelength of about 308 nm, with the optical fluid 55 being configured to transmit optical energy between the wavelengths of about 306 nm to about 310 nm. For some embodiments, the optical fluid may be water or saline. The distal section 42 of the liquid core laser ablation catheter 24 may be configured to be flexible enough to maneuver around the bends in a patient's vessel without kinking, yet be stiff enough to be able to push the liquid core laser ablation catheter 24 through a patient's body vessel while ablating blockages. The optical fluid 55 may be sealed within the interior lumen 53 of the catheter body tube 52 by the distal optical window 44 which is disposed in liquid sealed relation to a surface the catheter body tube 52 at a distal end thereof and an input optical window 45 which may be disposed in a liquid sealed relation with a proximal end of the catheter body tube 52 (see FIG. 2A). For some embodiments, it may be an outer surface of the insert segment 46 that is in liquid sealed relation to the inner surface 67 of the catheter body tube 52.

Figure 3:
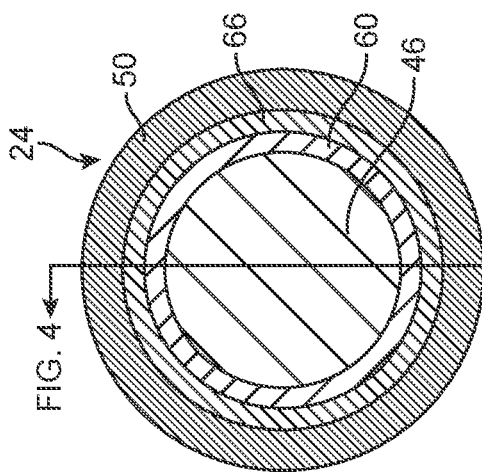
FIG. 3 is a transverse section view of the liquid core laser ablation catheter of FIG. 2.

For some embodiments of the liquid core laser ablation catheter 24, an exterior surface 54 of the insert segment 46 of the optical window 44 may be bonded to an interior window surface 56 of the window housing 50 using a suitable adhesive 58 as shown in FIG. 17. A distal section 60 of the catheter body tube 52 may be notched such that it can be coupled to a tube cavity 62 of the window housing 50 as shown in FIG. 4. A proximal portion 64 of the window housing 50 may be crimped to the distal section 60 of the catheter body tube 52 and to a portion of the insert segment 46 of the optical window. The crimped section may act to hermetically seal the interior lumen 53 which contains the optical fluid 55 from the environment which surrounds the liquid core laser ablation catheter 24. The window housing 50, the distal section 62 of the catheter body tube 52, the insert segment 46 of the distal optical window 44, and a cladding material 66 which encapsulates the insert segment 46 of the optical window 44 are shown in FIG. 3.

The expanded segment 48 of the distal optical window 44 may extend beyond a distal edge 68 of the window housing 50 as shown in FIG. 4. In some cases, it may be desirable for a distal edge of the expanded segment 48 to have a rounded or chamfered corner 45 as shown in FIG. 2. A diameter 70 of the expanded segment 48 may be greater than or equal to a diameter 72 of the window housing 44 as measured at the distal edge 68 of the window housing 44 in some cases. For some distal optical window embodiments 44 having an insert segment 46 with a core diameter of about 1 mm, the expanded segment 48 of the distal optical window 44 may have an outer diameter or transverse dimension 70 of about 1.1 mm to about 1.3 mm in some cases, in other cases the outer transverse dimension of the expanded segment 48 for such embodiments may be about 1.4 mm to about 1.6 mm. The distal optical window 44 may have an overall axial length 72 (including the axial length of the insert segment 46 and the expanded segment 48, see FIG. 12) selected to minimize stiffness of the distal section 42 of the liquid core laser ablation catheter 24 but still allow for sufficient beam expansion within the expanded segment 48 so as to fully fill the output surface 80 of the distal optical window 44 with optical energy 89. In some cases, the distal optical window 44 may have an axial length of less than about 10 mm, more specifically, less than about 8 mm, and even more specifically, less than about 6 mm, to allow the distal section 42 of the liquid core laser ablation catheter 24 to negotiate curves in when disposed within a patient's body lumen. For some embodiments of the distal optical window 44, the axial length of the expanded segment 48 may be about 0.5 mm to about 2 mm, and about 1 mm to about 2 mm for some embodiments. The ratio of the diameter 70 of the expanded segment 48 to the diameter of the insert segment 46 for a given distal optical window embodiment 44 may be about from about 1.1:1 to about 1.5:1 for some embodiments.

Figure 14:
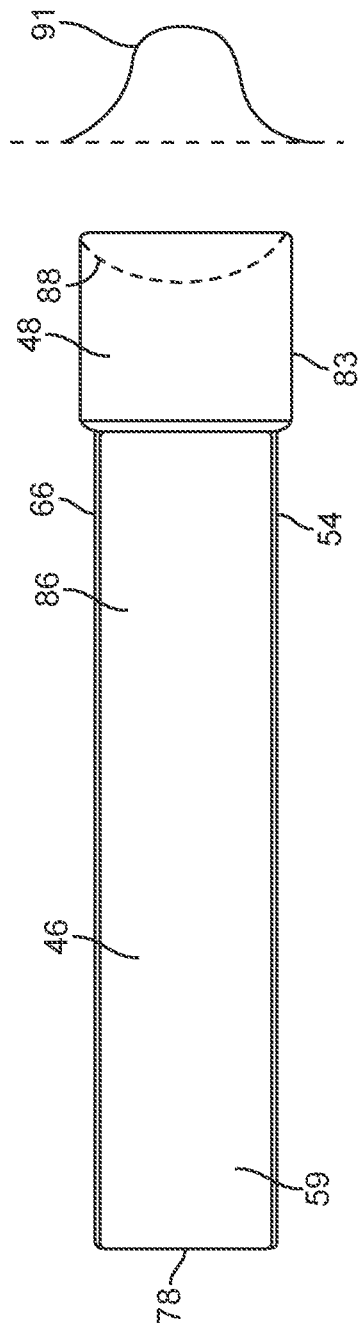
FIG. 14 is an elevation view of an optical window embodiment having an insert segment, an expanded segment, and a substantially concave output surface with rounded edges.

For some embodiments, the insert segment 46 of the distal optical window 44 which includes a waveguide fiber optic structure which may have a numerical aperture (NA) in the waveguide structure greater than or equal to a NA of the optical fluid 55 in combination with the inner surface 76 of the catheter body tube 52 in order to minimize optical losses at the transition between optical fluid 55 and the distal optical window 44. That is, the optical fluid 55 disposed within the interior lumen 53 of the catheter body tube 52 forms a waveguide structure in combination with an inner layer or surface 76 of the catheter body tube 52 based on the respective IRs of the optical fluid 55 and inner layer 67 so as to include a waveguide structure for the catheter body tube 52 having an NA that is dependent upon those respective IRs. Generally speaking, a first IR of the inner layer 67 is less than a second IR of the optical fluid 55 to produce a waveguide configuration. In some cases, the distal optical window 44 may include a high NA optical fiber or a silica rod which is coated with a relatively low numerical index of refraction material such as an amorphous fluoropolymer coating or a dielectric coating that is transparent or reflective of the optical energy laser pulse, which may include an ultraviolet energy pulse. FIGS. 13 and 14 depict embodiments of the distal optical window 44 with different tip shapes. The distal optical window which is depicted in FIGS. 2, 4, and 12 features a substantially flat output surface 80 which is disposed at a distal end 81 of the expanded segment 48. FIG. 13 depicts a distal optical window embodiment 82 which incorporates a convex output surface 84, and FIG. 14 depicts a distal optical window embodiment 86 which incorporates a concave output surface 88. Any liquid core laser ablation catheter embodiment discussed herein may incorporate any such distal optical window shape configuration discussed herein.

Figure 19:
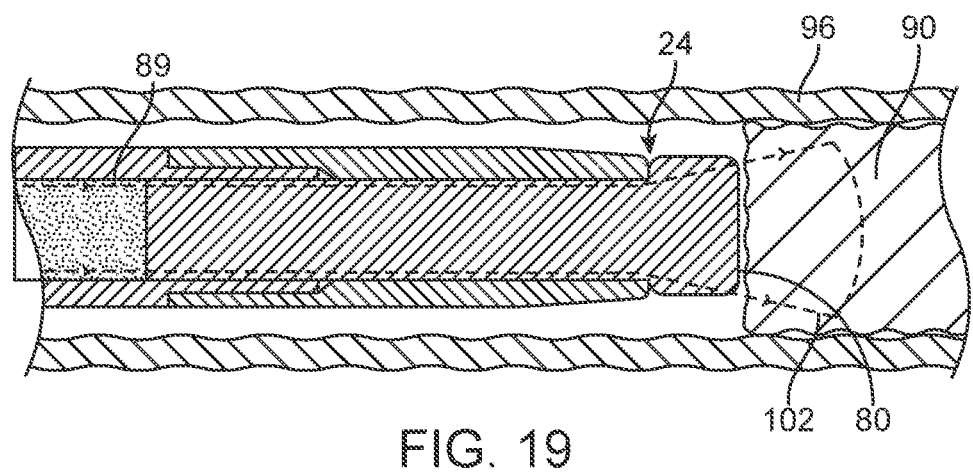
FIG. 19 is an elevation view in longitudinal section of the liquid core laser ablation catheter embodiment of FIG. 4 cutting through a lesion in a body lumen.
Figure 20:
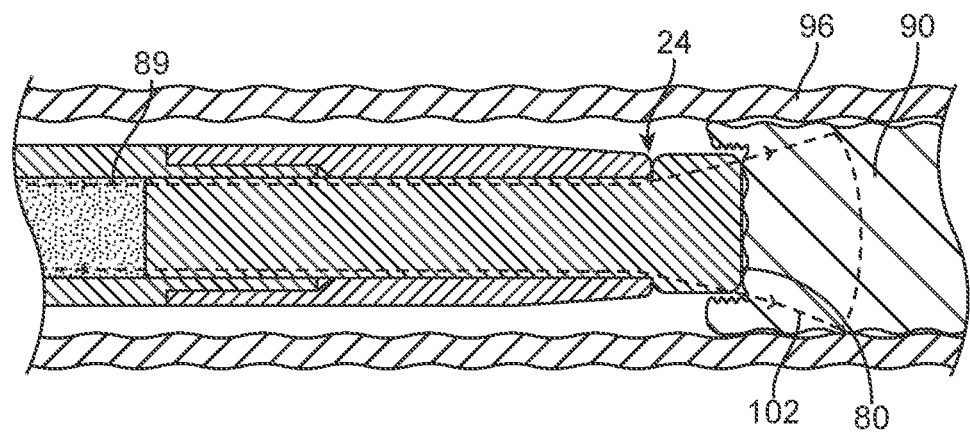
FIG. 20 is an elevation view of the liquid core laser ablation catheter of FIG. 19 being advanced into target tissue of the lesion during ablation.

In use, the liquid core laser ablation catheter 24 may function to ablate target materials or tissue as follows. Referring to FIGS. 1 and 12, optical energy 89 transmitted from the laser source 12 enters the laser coupler 26 of the liquid core laser ablation catheter and is then transmitted into the optical fluid 55 which is disposed within the interior lumen 53 of the catheter body tube 52. The optical energy 89 is then transmitted through the optical fluid 55 along the working length 40 of the liquid core laser ablation catheter 24, with an interior surface 76 of interior lumen 53 of the catheter body tube 52 acting in conjunction with the optical fluid 55 to form a liquid core waveguide. The optical energy 89 then enters an input surface 78 of the distal optical window 44, and is transmitted through the insert segment 46 and expanded segment 48 of the distal optical window 44 as shown in FIG. 2, and then exits the optical window 44 through the output surface 80 of the distal optical window 44 and into target material 90 (see FIG. 19). As the optical energy 89 ablates the target material 90, the distal optical window 44 may be distally advanced into the cavity being formed into the target material 90 as shown in FIG. 20 in order to maintain contact or near contact between the output surface 80 and the target material 90.

Figure 5:
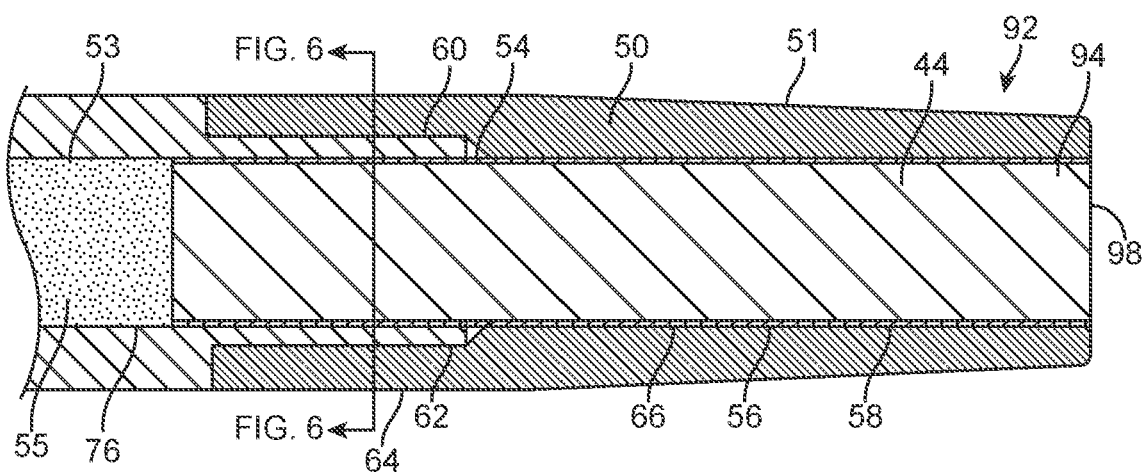
FIG. 5 is a longitudinal section view of a distal section of a liquid core laser ablation catheter embodiment which includes an optical window having a constant diameter, a tapered window housing, a catheter body tube, and an optical fluid disposed within the catheter body tube.
Figure 6:
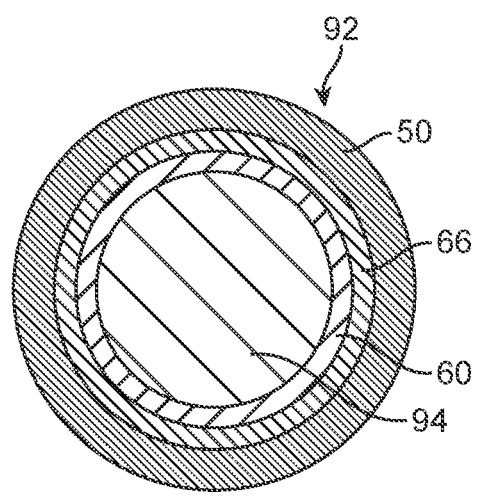
FIG. 6 is a transverse section view of the liquid core laser ablation catheter of FIG. 5.
Figure 11:
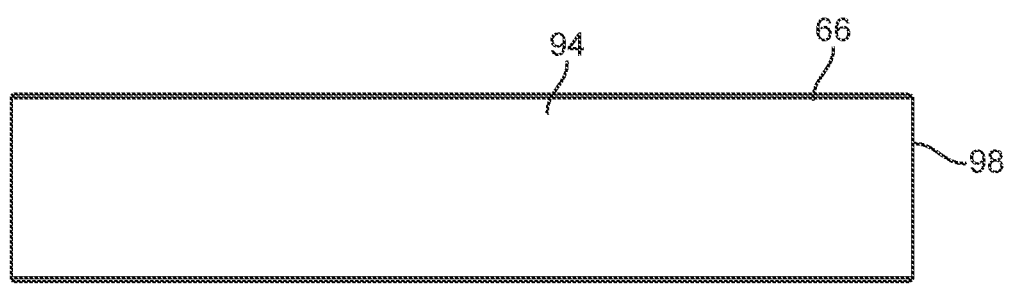
FIG. 11 is an elevation view of a fiber optical window embodiment having a constant diameter with a flat polished distal surface with substantially non-rounded edges.
Figure 18:
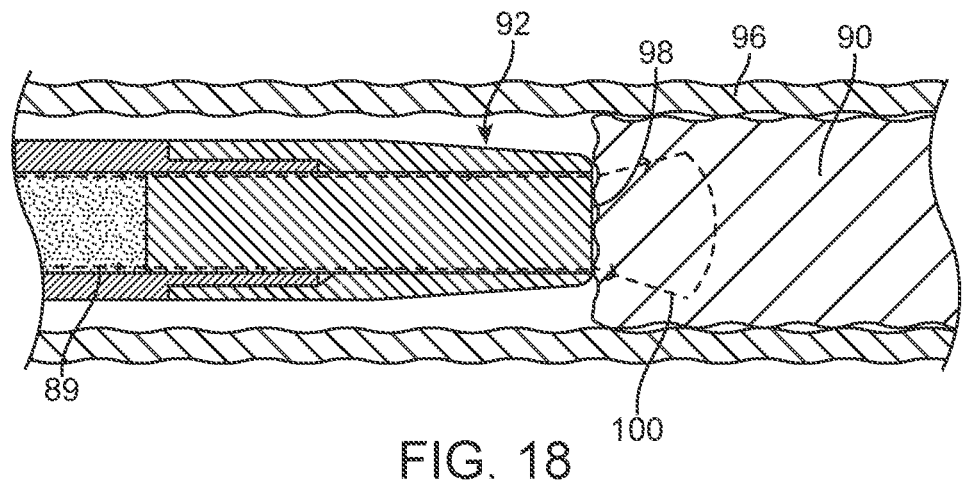
FIG. 18 is an elevation view in longitudinal section that shows the liquid core laser ablation catheter embodiment of FIG. 5 cutting through a lesion is a body lumen.

An embodiment of a liquid core laser ablation catheter 92 that does not include an expanded segment on a distal optical window is shown in FIGS. 5, 6, and 18. The liquid core laser ablation catheter 92 may incorporate a constant diameter distal optical window 94 which is depicted in FIG. 11. The constant diameter distal optical window 94 may be bonded into a tapered window housing 50 with an adhesive 58 as shown in FIG. 16. The configurations, dimensions, materials, and functions of elements of the liquid core laser ablation catheter 92 may be substantially similar to similar elements of the liquid core laser ablation catheter 24 which has been discussed herein. The liquid core laser ablation catheter 92 is shown in order to illustrate the improved cutting ability of the liquid core laser ablation catheter embodiments 24 having a distal optical window 44 which incorporates an expanded segment 48 as shown in FIGS. 19 and 20.

FIG. 18 depicts the liquid core laser ablation catheter 92 disposed within a patient lumen 96 ablating target tissue material 90 with optical energy 89. The optical energy 89 exits an output surface 98 of the constant diameter optical window 94 within a first cone angle 100. For contact cutting systems, a hole the size of the optical energy beam 89 is created at the output surface 98 of liquid core laser ablation catheter 92. As shown, this hole may be smaller in transverse dimension than the liquid core laser ablation catheter 92. FIG. 19 similarly depicts the liquid core laser ablation catheter 24 disposed within a patient lumen 96 ablating target tissue material 90 with optical energy 89. The optical energy 89 exits an output surface 80 of the expanded optical window 44 within a second cone angle 102. As can be seen in FIGS. 18 and 19, the expanded segment 48 of the optical window 44 allows the optical energy 89 to diverge prior to exiting the output surface 80. Thus the second cone angle 102 of optical energy 89 produced by liquid core laser ablation catheter 24 provides a greater cutting area than the first cone angle 100 of optical energy 89 produced by liquid core laser ablation catheter 92. This allows the liquid core laser ablation catheter 24 to ablate a hole large enough for the distal section 50 of the liquid core laser ablation catheter 24 to readily follow into the newly created lumen.

Figure 7:
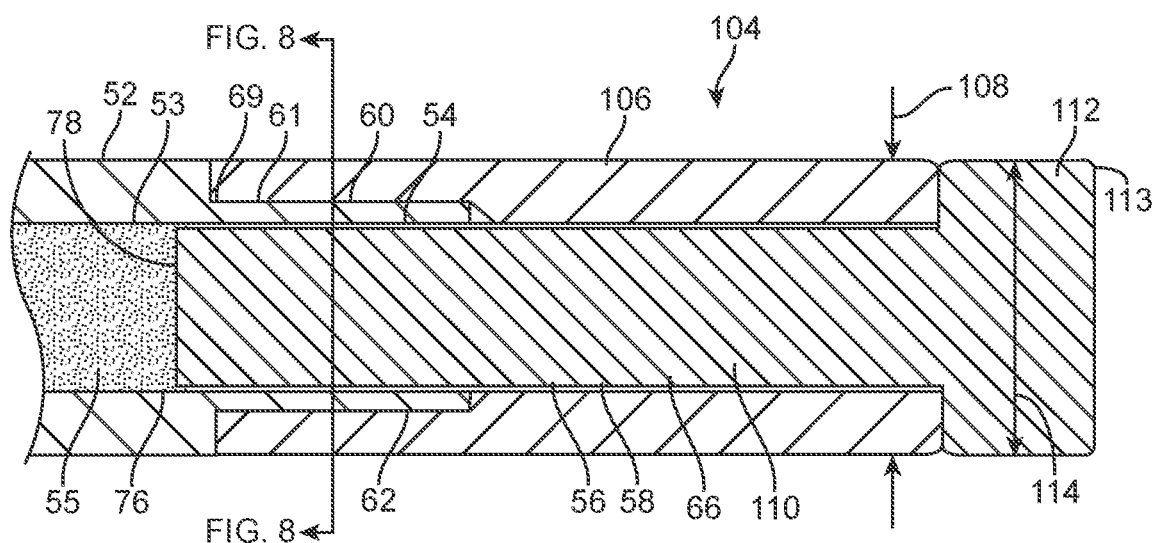
FIG. 7 is a longitudinal section view of a liquid core laser ablation catheter embodiment distal section which includes an optical window having an insert segment and an expanded segment with a rounded and/or chamfered distal edge, a non-tapered window housing, a catheter body tube, and an optical fluid disposed within the catheter body tube.
Figure 8:
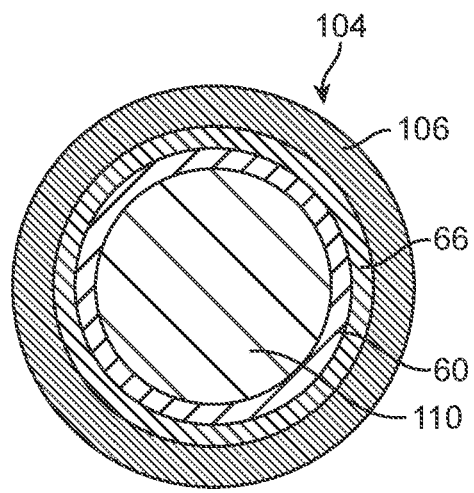
FIG. 8 is a transverse section view of the liquid core laser ablation catheter embodiment of FIG. 7.

FIGS. 7 and 8 depict an embodiment of a liquid core laser ablation catheter 104 which features a non-tapered window housing 106. That is, an outer diameter 108 of the window housing 106 may be constant along the length of the window housing 106. The liquid core laser ablation catheter 104 may incorporate a distal optical window 110 which has an expanded segment 112 having an outer diameter 114 that is equal to or greater than the outer diameter 108 of the window housing 106. As with the distal optical window embodiment 44 of FIG. 2, the distal edge of the expanded segment 112 may have a rounded or chamfered corner 113 in order to facilitate smooth passage of the distal end of the catheter through a patient's vessels. Other than the configuration of the window housing 106, the configurations, dimensions, materials, and functions of elements of the liquid core laser ablation catheter 104 may be substantially similar to or the same as similar elements of the liquid core laser ablation catheter 24 discussed herein.

Figure 9:
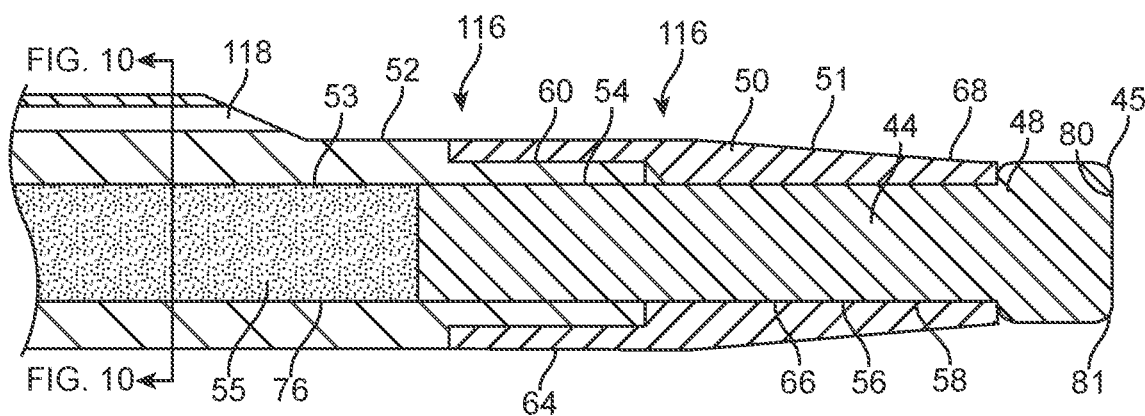
FIG. 9 is a longitudinal section view of a liquid core laser ablation catheter embodiment distal section which includes an optical window having an insert segment and an expanded segment with a substantially flat output surface and a rounded distal edge, a tapered metal housing, a catheter body tube, an optical fluid disposed within the catheter body tube, and an eccentric guide wire lumen which is disposed on an exterior surface of the catheter body tube.
Figure 10:
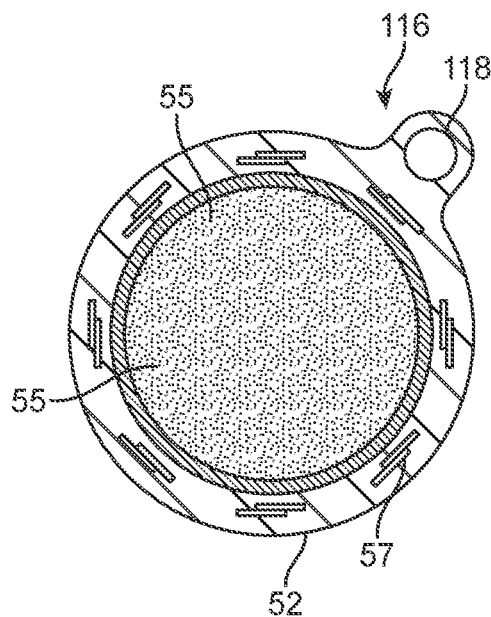
FIG. 10 is a transverse section view of the liquid core laser ablation catheter embodiment of FIG. 9.

FIGS. 9 and 10 depict another embodiment of a liquid core laser ablation catheter 116 that incorporates an eccentric guidewire lumen 118 which is disposed on the periphery or outer surface of the catheter body tube 52 and extends axially along the outer surface of the catheter body tube 52. The guidewire lumen 118 is configured to couple to a suitable guidewire, such as a coronary angioplasty type guidewire, thereby allowing for the ablation of eccentric target tissue materials 90 utilizing the liquid core laser ablation catheter 116. Other than the configuration of the eccentric guidewire lumen 118, the configurations, dimensions, materials, and functions of elements of the liquid core laser ablation catheter 116 may be substantially similar to or the same as similar elements of the liquid core laser ablation catheter 24 which has been previously discussed.

Pulsed ultraviolet excimer laser ablation catheter embodiments which have been discussed herein may be configured to remove various types of atheroma by photochemical, photo-thermal and photo-acoustic processes. With this ablative method the irradiated tissue may be removed with little to no thermal damage to the edges of the lumen wall of the patient, because the nanosecond pulse duration of the ultraviolet pulsed excimer laser currently used for this application is at time scales much less than the thermal diffusion time of the absorbed optical energy. The pulsed optical energy from the laser must be delivered inside the body lumen with a flexible fiber optic or waveguide that can pass the tortuosity of the arterial anatomy of a patient's body to get to the site of the blockage. A single fiber optic might present an efficient cutting surface, but because the catheter size is in the range of 1 mm to 2.5 mm diameter for the ablation surface, these single fibers at this diameter are too stiff for percutaneous use in a patient's body lumen.

Some previous embodiments of ablation catheters use many small diameter fiber optics, typically with cores having diameters of about 50 microns in quantities of about 100 fiber optics to about 300 fiber optics, arranged in a bundle to provide a flexible ablation catheter in a 1 mm to 2.5 mm diameter. Unfortunately, this cutting surface configuration may produce a "Swiss cheese" type dead space geometry due to the cladding, packing factor of the multiple fibers, and the outer tube wall thickness. It has been demonstrated that this configuration does not cut as efficiently as a surface with less dead space (such as an ablation catheter which is configured with a single fiber optic) and requires more energy and a higher pulse rate to ablate target tissue.

As has been discussed, an improvement to multiple fiber laser ablation catheters is the liquid core laser ablation catheter 92 with a solid distal optical window 94 which is disposed at a distal section 60 of the liquid core laser ablation catheter 92. However, there may still be some residual dead space due to the cladding material 66 on the distal optical window 94 and the catheter body tube 52 that contains the optical fluid 55 and the distal optical window 94. Although this ablation catheter 92 configuration requires lower pulsed optical energy to ablate through target material, the ablation hole which is created may be slightly smaller than the outside surface of the ablation catheter 92 in some cases. This may result in resistance to passage of the ablation catheter 92 through target material such as a lesion, especially for a non-compliant lesion such as calcified lesions.

Laser ablation catheters which incorporate the window housing 50 which includes the tapered section 51 may have improved maneuvering through tortuous lesion sites when compared to ablation catheters which do not have tapered window housings. This is due to the fact that laser ablation catheters which incorporate the window housing 50 which includes the tapered section 51 have a reduced profile at the catheter distal section 60 which can more easily pass through tortuous lesion sites within the vasculature of a patient.

The addition of the distal optical window 44 which incorporates the expanded segment 48 as has been discussed may further improve the ability of a given laser ablation catheter (such as liquid core laser ablation catheter 24) to ablate through target material 90. Optical energy 89 which enters the distal optical window 44 may be transmitted through the insert segment 46 of the optical window 44 (where it may be optically contained by a cladding material 66) and into the expanded segment 48, that does not include a cladding layer to serve as a waveguide, where it may diverge and exit the expanded segment 48 through the output surface 80 of the distal optical window 44. The surface area of the output surface 80 of the distal optical window 44 may in some cases be greater than or equal to the area of elements which are disposed at the distal section 60 of the respective laser ablation catheter such as the window housing 50 or the catheter body tube 52.

Some ablation catheters which utilize the distal optical window 44 having an insert segment 46 and an expanded segment 48 may have no dead space at the output surface 80 of the distal optical window 44. As an example consider an ablation experiment conducted utilizing two ablation catheters which incorporate the same size 5 French (1.57 mm) catheter body tube 52 and a 1.22 mm tapered tip diameter at the distal end. A first ablation catheter incorporated a 1 mm diameter distal optical window (constant diameter distal optical window similar to embodiment 92 in FIG. 18) and a second ablation catheter incorporated an distal optical window (enlarged head distal optical window similar to embodiment 24 in FIG. 19) having an expanded section 48 with a diameter of 1.22 mm. Ablation experiments were performed using each configuration, with the enlarged segment 48 configuration of laser ablation catheter 24 producing a larger ablation hole than the constant diameter configuration exemplified in laser ablation catheter 92 and the enlarged segment 48 configuration of laser ablation catheter 24 being easier to ablate through phantom targets.

The area of the output surface of a given distal optical window is proportional to the diameter of the distal optical window squared. Thus for the given example the distal optical window 44 configured with the expanded segment 48 (1.22 mm diameter) produces a 49 percent larger ablation area (output surface 80) for the same diameter optic window 94 (1 mm diameter core) with a constant diameter on the same size catheter (5 French). In some cases, the pulse energy from the laser may need to be increased in order to achieve the appropriate energy fluence over the larger output surface 80 of the expanded segment 48 of the distal optical window 44.

As has been discussed, the expanded segment 48 of the distal optical window 44 may be configured with an output surface 80 which has a surface area which is equal to or greater than a surface area of a cross section of the ablation catheter 24. For some embodiments for treating peripheral arterial disease where tortuosity is less severe, the distal optical window 44 may incorporate an insert segment 46 (typically 5 to 8 mm length for some embodiments) which may be formed from a single length of feed fiber optic. The insert segment 46 may be disposed within the window housing 50 and/or the catheter body tube 52 of the liquid core laser ablation catheter 52. For some embodiments, a proximal portion 59 of the insert segment 46 may extend proximally from the interior of the window housing 50 and into the inner lumen 53 of the catheter body tube 52 as shown in FIG. 4. The distal optical window 44 may also include expanded segment embodiments 48 having enlarged diameter 70 that is equal to or larger than the distal portion 68 diameter 72 of the ablation catheter 24.

In some cases the distal optical window 44 may be formed from a suitably configured feed fiber optic. The expanded segment 48 may be formed by melting the cladding material 66 of the feed fiber optic into the inner core of the feed fiber optic within a distal segment of the feed fiber optic, and then shaping the glass within the distal segment into the expanded segment 48 after shaping the entire distal optical window 44 may be annealed to reduce or remove any stress in the material of the distal optical window 44. After being formed, the distal optical window 44 may be secured (using any suitable adhesive for example) into a suitably configured window housing 50 (as shown in FIG. 17). The assembly of the distal optical window 44 and window housing 50 may then be secured to a suitably configured catheter body tube 52. In some cases, the assembly of the distal optical window 44 and window housing 50 may be crimped to the catheter body tube 52 onto the insert segment 26 of the distal optical window 44. As has been discussed, the optical fluid 55 may be disposed within the inner lumen 53 of the catheter body tube 52. An input optical window 45 may be inserted into the inner lumen 53 of the proximal end of the catheter body tube 52 in sealed relation to the inside surface of the inner lumen of the catheter body tube 52. For some embodiments, the input optical window may be made from an ultraviolet grade material such as silica, sapphire or the like that are configured to efficiently transmit ultraviolet optical energy. A laser connector 26 may then be attached to the proximal section 28 of the liquid core laser ablation catheter 24.

Some embodiments of the window housing 50 may include at least one crimp ridge 67 which may be disposed circumferentially about and extend into the tube cavity 62 of the window housing 50. Each crimp ridge 67 may assist in securing the window housing 50 to the catheter body tube 52 after the crimping process. Each crimp ridge 67 may be configured as an annular protrusion which extends from an inner surface of the crimped portion of the tube cavity 62 of the window housing 50 (see FIG. 4) and into the nominal tube cavity 62. The crimp ridge 67 which is depicted in FIG. 4 is configured with a radiused profile, however embodiments of crimp ridges 67 may be configured with any suitable profile such as a rectangular profile or a triangular profile.

Figure 15:
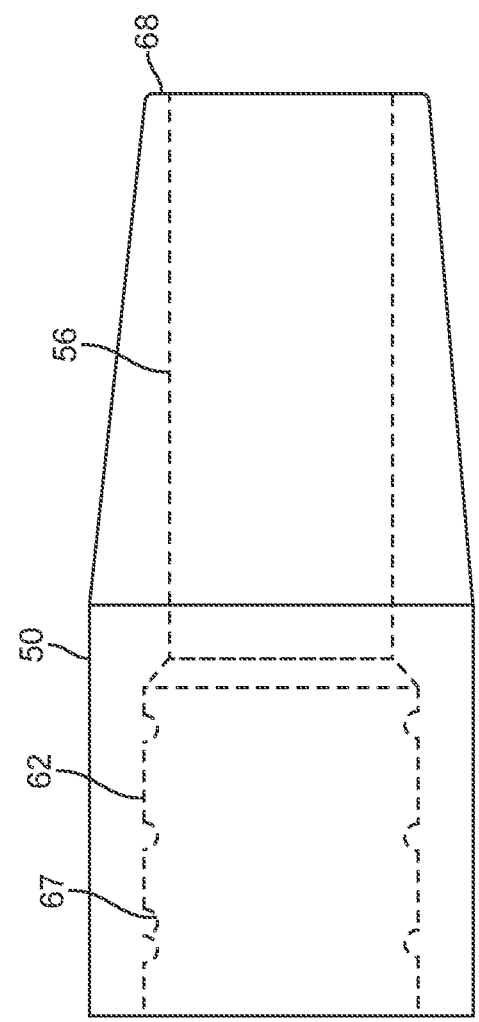
FIG. 15 is an elevation view of a tapered metal window housing embodiment.

For some embodiments, multiple crimp ridges 67 may be disposed such that they are axially spaced along the interior surface of the tube cavity 62 as shown in FIGS. 15-17. Some embodiments of the window housing 50 may be configured with about 1 to about 5 crimp ridges. For window housing embodiments 50 which incorporate multiple crimp ridges 67, the crimp ridges 67 may have an axial spacing of about 0.38 mm to about 0.64 mm. The crimping process which has been previously discussed may result in the penetration of each crimp ridge 67 of a respective window housing 50 into the wall material of the distal section 60 of the catheter body tube 52 as shown in FIG. 4. The penetration of each crimp ridge 67 into the wall material of the distal section 60 of the catheter body tube 52 may result in a mechanical bond between the window housing 50, the distal optical window 44, and the catheter body tube 52. In this manner the penetration of each crimp ridge 67 into the distal section 60 of the catheter body tube 52 may act to prevent relative translational motion between the window housing 50, the distal optical window 44, and the catheter body tube 52. Any embodiment of window housings which are discussed herein may be configured with at least one crimp ridge 67.

Thus, the laser coupler 26 may be optically coupled to the optical fluid 55 which is disposed within the inner lumen 53 of the catheter body tube 52. The optical fluid 55 is in turn optically coupled to the input surface 78 of the distal optical window 44. The input surface may in turn be optically coupled to the output surface 80 of the distal optical window 44 by the insert segment 46 and the expanded segment 48 of the distal optical window 44. As has been discussed, cladding material 66 may be disposed on the outside surface 54 of the insert segment 46 with the cladding material forming a waveguide configuration facilitating the transmission of optical energy 89 through the insert segment 46.

In some cases, the catheter body tube 52 may be a fluoropolymer tube. The distal end 60 of the fluoropolymer tube 52 may be notched to a reduced outer diameter to attach the window housing 50 such that a proximal portion 64 of the window housing 50 matches the outside diameter of the catheter body tube 52 after the window housing 50 has been crimped to the catheter body tube 52. In some cases, the window housing 50 which secures the distal optical window 44 may also act as a radiopaque marker to locate the distal portion 38 of the liquid core laser ablation catheter 24 during a procedure which utilizes x-ray fluoroscopy.

The typical NA of waveguide functioning portions of distal optical window embodiments 44 formed from ultraviolet transmitting silica over silica fiber optics may be about 0.22, thus providing a full cone angle of optical energy 89 of about 25 degrees. The NA of the feed fiber within the insert segment 46 of the distal optical window 44 may transmit through the expanded segment 48 of the distal optical window 44. In some cases, the cladding material 66 may be removed from the expanded segment 48 of the distal optical window 44 during the formation of the distal optical window 44. In some cases the optical energy 89 which is transmitted through the insert segment 46 (which may be configured as an optical feed fiber) of the distal optical window 44 expands in a full cone angle into the expanded segment 48 as determined by the numerical aperture of the feed fiber which for some embodiments may include a full cone angle of optical energy 89 of about 25 degrees as shown in FIG. 12.

The distribution 91 of the optical energy 89 at the output surface 80 of the distal optical window 44 may be somewhat Gaussian (again see FIG. 12) with most of the optical energy 89 located in the central region and with lower optical energy at the edges. The degree of central concentration is correlated to the overall length 74 of the expanded segment 48, because the light may radially expand within the material of the expanded segment 48 by a full cone angle of about 25 degrees in some cases when it enters the expanded segment 48 which may have no cladding material 66. In some cases the axial length 74 of expanded segment 48 may be minimized in order to maintain catheter tip flexibility, and because there may be no cladding material 66 to contain the optical energy 89 in the expanded segment 48 of the distal optical window 44. If there are too many internal reflections of the optical energy 89 within the expanded segment 48, due to, for example, an unnecessarily long axial length of the expanded segment 48, optical energy 89 may escape from an outer surface 83 of the expanded segment 48. The overall length 74 of this expanded segment 48 may thus generally be a compromise between these factors.

For some embodiments the catheter body tube 52 may be attached to the window housing 50 by crimping the proximal portion 64 of the window housing 50 onto a distal portion 60 of the catheter body tube 52 and a respective proximal portion 59 of the distal optical window 44. In this manner the distal portion 60 of the catheter body tube 52 is crimped to the proximal portion 59 of the distal optical window 44 by the proximal portion 64 of the window housing 50 which may produce a liquid tight seal between the catheter body tube 52 and the distal optical window 44 such that the inner lumen 53 is sealed at the distal end of the catheter body tube 52 by the distal optical window 44. A tube outer surface 61 of the catheter body tube 52 may be configured to couple to a housing inner surface 69 of the window housing 50. In some cases, the outer surface 61 at the distal portion 60 may be stepped to a reduced outer diameter such that after crimping the window housing 50 over the distal portion, the transition of the outer surface between the catheter body tube 52 and the window housing 50 is smooth. For some embodiments, the distal portion 60 of the catheter body tube 52 may be bonded into the proximal portion 64 of the window housing 50 with a suitable adhesive 58 such as medical grade class VI epoxy for fiber optics, with the adhesive 58 being disposed between the outer surface 61 of the catheter body tube 52 and housing inner surface 69. In some cases, an inner lumen of the proximal portion 64 of the window housing 50 may be expanded to an inside diameter which is greater than an outside diameter of the distal portion 60 of the catheter body tube 52 in order to facilitate assembly of the device and couple to the distal portion 60 of the catheter body tube 52. In turn, as discussed above, the distal portion 60 of the catheter body tube 52 may optionally be notched or suitably tapered in order to couple to the proximal portion 64 of the window housing 50 thereto.

In some cases, it may be desirable to have the distal optical window 44 configured as a modified fiber optic because a distal optical window which is configured as a bare ultraviolet silica rod would fail optically as a waveguide. This is because either the adhesive 58 or the window housing 50 inner surfaces (56, 69) of the window housing 50 would absorb the optical energy 89 configured as ultraviolet light, or any other suitable wavelength range of optical energy, which is transmitted through the distal optical window 44 for such an embodiment, as it would not be refracted from the interface between the distal optical window 44 and the adhesive 58. This is because such an adhesive 58 is not likely to be configured to transmit or refract the optical energy 89. In order to properly function as a waveguide, such a bare window substrate would need to be coated with a low index of refraction coating, a dielectric, reflective metallic coating or the like. In some cases the axial length 74 of the expanded segment 48 of the distal optical window 44 may be only about 1 mm, and the exit angle of the optical energy 89 emitted from the insert segment 46 may have a full cone angle of about 25 degrees into the expanded segment 48 (as shown in FIG. 12). Thus, most of the optical energy 89 for an embodiment with a bare insert segment 46 would escape through outer side surfaces the insert segment 46 of the distal optical window 44 which is configured with no cladding material 66, and would be absorbed by the window housing 50.

In some cases it may be desirable to improve the distribution 91 of the optical energy 89 (see FIG. 12) within the expanded segment 48 of the distal optical window 44 by using distal optical window embodiments 44 with insert segment embodiments 46 having a silica over silica fiber optic structure with a large numerical aperture. Distal optical window embodiments 44 including a large numerical aperture silica over silica fiber optic structure may produce greater divergence for optical energy 89 being emitted from the core of the insert segment 46 into the material of the expanded segment 48 of the distal optical window 44. As an example, a fiber optic structure with a silica over silica core-cladding arrangement for the insert segment 46 with an NA of 0.30 yields a cone angle of about 35 degrees for optical energy emitted from the insert segment 46 into the expanded segment 48 that will have improved expansion within the expanded segment 48 of the distal optical window 44. In addition, a better match of the respective indices of refraction of the optical fluid 55 and material of the distal optical window 44 may also be useful to reduce coupling losses at the interface of two materials with differing indices of refraction. The convex output surface 84 of the expanded segment 48 of the distal optical window embodiment of FIG. 13 may act to concentrate the optical energy 89 emitted from the expanded segment 48 to produce a higher energy fluence in the middle of the beam relative to the energy fluence of the optical beam 89 in the insert segment 46 portion of the distal optical window embodiment 44. The concave output surface 88 of the distal optical window embodiment which is depicted in FIG. 14 may act to expand the optical energy 89 emitted from the center of the expanded segment 48 to the edges of the expanded segment 48, in order to smooth out the Gaussian-like energy distribution 91 such as may be generated from a flat output surface 80 as shown in FIG. 12.

For some liquid core laser ablation catheter embodiments, the process of crimping the window housing 50 onto the catheter body tube 52 and the distal optical window 44 offers improved adhesion strength over some previous embodiments particularly since adhesives do not typically bond well onto fluoropolymers such as Teflon® or FEP. The distal optical window 44 may be bonded to the window housing 50 as has been previously discussed, and the proximal section 64 of the window housing 50 may be configured to couple to a distal section 60 of the catheter body tube 52. The proximal section 64 of the window housing 50 may then be crimped onto the distal section 60 of the catheter body tube 52 and the insertion segment 46 of the distal optical window 44 by any suitable means. For example, the crimping process may be accomplished by a suitably configured crimping machine.

The compression of the window housing 50 onto the catheter body tube 52 and the insert segment 46 of the distal optical window 44 may act to form a hermetic seal between the window housing 50 and the catheter body tube 52 in some cases. The crimped configuration, particularly with the use of internal ridges 67 that penetrate an outer wall of the distal section 60 of the catheter body tube 52, may also improve adhesion strength of the junction between the window housing 50, the distal optical window 44 and the catheter body tube 52. The strength of this junction may in some instances be indicated by destructive pull force testing which may be performed on multiple such assemblies. In some cases the ridges 67 upon being embedded in the wall material of the distal section 60 of the catheter body tube 52 may mechanically capture the distal section 60 to the window housing 50 which may be particularly useful for embodiments using fluoropolymers (such as FEP) for the catheter body tube 52 which may have a very low coefficient of friction and be generally slippery and ill suited for adhesive bonding. Improved adhesion strength may be achieved with the use of a distal optical window embodiment 44 which is formed from a fiber optic. The distal optical window 44 formed from a fiber optic may be configured with a length which is long enough to achieve a good hermetic seal, but with the overall length 74 of the distal optical window 44 being axially short enough to keep the distal section 60 of the ablation catheter 24 flexible so as to maintain the capability of going through curves in a patient's anatomy such as vascular lumens and the like.

The entirety of each patent, patent application, publication and document referenced herein hereby is incorporated by reference. Citation of the above patents, patent applications, publications and documents is not an admission that any of the foregoing is pertinent prior art, nor does it constitute any admission as to the contents or date of these publications or documents.

Modifications may be made to the foregoing without departing from the basic aspects of the embodiments discussed. Although embodiments have been described in substantial detail with reference to one or more specific embodiments, those of ordinary skill in the art will recognize that changes may be made to the embodiments specifically disclosed in this application, yet these modifications and improvements are within the scope and spirit of the disclosure.

Embodiments illustratively described herein suitably may be practiced in the absence of any element(s) not specifically disclosed herein. Thus, for example, in each instance herein any of the terms "comprising," "consisting essentially of," and "consisting of" may be replaced with either of the other two terms. The terms and expressions which have been employed are used as terms of description and not of limitation and use of such terms and expressions do not exclude any equivalents of the features shown and described or portions thereof, and various modifications are possible. The term "a" or "an" can refer to one of or a plurality of the elements it modifies (e.g., "a reagent" can mean one or more reagents) unless it is contextually clear either one of the elements or more than one of the elements is described. Thus, it should be understood that although embodiments have been specifically disclosed by representative embodiments and optional features, modification and variation of the concepts herein disclosed may be resorted to by those skilled in the art, and such modifications and variations are considered within the scope of this disclosure.

Certain embodiments of the technology are set forth in the claim(s) that follow(s).

What is claimed is:

1. A laser ablation catheter to ablate blockages in body lumens using high energy laser pulses, comprising:
   a liquid filled waveguide including an elongate catheter body tube having an inner surface with a first index of refraction and a biocompatible ultraviolet transparent optical fluid disposed within and completely filling an inner lumen of the elongate catheter body tube, with the optical fluid having a second index of refraction which is greater than the first index of refraction; and
   an ultraviolet grade elongated distal optical window disposed in liquid sealed relation to a surface of the elongate catheter body tube at a distal end of the elongate catheter body tube, the distal optical window including:
      an insert segment which is disposed within a distal section of the elongate catheter body tube and which comprises an ultraviolet grade material,
      a layer of material disposed about an outer surface of the insert segment which includes an index of refraction lower than an index of refraction of the material of the insert segment or a reflective material, and
      an expanded segment which is disposed distally of the insert segment, which comprises an ultraviolet grade material configured to efficiently transmit ultraviolet optical energy for ablation of blockages in body lumens which has an outer diameter which is greater than an outer diameter of the insert segment, which has an output surface that has an area which is equal to or greater than an area of a transverse section of the elongate catheter body tube proximally adjacent the distal optical window and which has an axial length sufficient to allow optical energy expansion within the expanded segment such that optical energy emitted from the output surface ablates a hole in target tissue having a diameter equal to or greater than an outer diameter of the elongate catheter body tube proximally adjacent the distal optical window.

2. The laser ablation catheter of claim 1 wherein the insert segment comprises silica or sapphire.

3. The laser ablation catheter of claim 1 wherein the layer of material disposed about the outer surface of the insert segment comprises the inner layer of the catheter body tube.

4. The laser ablation catheter of claim 3 wherein the inner layer of the catheter body tube comprises an amorphous fluoropolymer.

5. The laser ablation catheter of claim 1 wherein the layer of material disposed about the outer surface of the insert segment comprises a material with an index of refraction lower than an index of refraction of the material of the insert segment and further comprises an amorphous fluoropolymer.

6. The laser ablation catheter of claim 1 wherein the layer of material disposed about the outer surface of the insert segment comprises a reflective material and further comprises a dielectric material or metal.

7. The laser ablation catheter of claim 1 wherein the expanded segment is not configured to act as a waveguide.

8. The laser ablation catheter of claim 1 further comprising an input optical window disposed in liquid sealed relation with a proximal end of the catheter body tube.

* * * * *